United States Patent
Chobotov et al.

(10) Patent No.: US 10,682,222 B2
(45) Date of Patent: Jun. 16, 2020

(54) MODULAR VASCULAR GRAFT FOR LOW PROFILE PERCUTANEOUS DELIVERY

(71) Applicant: TriVascular, Inc., Santa Rosa, CA (US)

(72) Inventors: Michael V. Chobotov, Santa Rosa, CA (US); Robert G. Whirley, Santa Rosa, CA (US); Joseph W. Humphrey, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 16/231,219

(22) Filed: Dec. 21, 2018

(65) Prior Publication Data

US 2019/0117372 A1 Apr. 25, 2019

Related U.S. Application Data

(63) Continuation of application No. 12/245,620, filed on Oct. 3, 2008, now Pat. No. 10,159,557.

(Continued)

(51) Int. Cl.
*A61F 2/07* (2013.01)
*A61F 2/954* (2013.01)
(Continued)

(52) U.S. Cl.
CPC .............. *A61F 2/07* (2013.01); *A61F 2/954* (2013.01); *A61F 2/966* (2013.01); *A61F 2/89* (2013.01); *A61F 2002/067* (2013.01); *A61F 2002/075* (2013.01); *A61F 2002/8486* (2013.01); *A61F 2002/9511* (2013.01); *A61F 2220/005* (2013.01); *A61F 2220/0058* (2013.01); *A61F 2250/0003* (2013.01); *A61F 2250/0069* (2013.01)

(58) Field of Classification Search
CPC .. A61F 2/07; A61F 2/954; A61F 2/966; A61F 2/89; A61F 2002/075; A61F 2002/8486; A61F 2002/9511; A61F 2250/003; A61F 2250/0069
See application file for complete search history.

(56) References Cited

U.S. PATENT DOCUMENTS 3,076,737 A 2/1963 Roberts
3,540,431 A 11/1970 Uddin
(Continued)

FOREIGN PATENT DOCUMENTS

CA 2438087 3/2001
DE 19624642 1/1998
(Continued)

OTHER PUBLICATIONS

US 6,413,270 B1, 07/2002, Thornton et al. (withdrawn)
(Continued)

*Primary Examiner* — Christopher D. Prone
*Assistant Examiner* — Tiffany P Shipmon
(74) *Attorney, Agent, or Firm* — Foley & Lardner LLP

(57) ABSTRACT

A hybrid modular endovascular graft wherein a main graft is sized to span at least a portion of a target vessel lesion in a large percentage of patients. Graft extensions may be secured to the main graft to extend the main graft and provide a sealing function for some applications.

22 Claims, 16 Drawing Sheets

US 10,682,222 B2

Page 2

Related U.S. Application Data

(60) Provisional application No. 60/977,617, filed on Oct. 4, 2007.

(51) Int. Cl.
  *A61F 2/966* (2013.01)
  *A61F 2/06* (2013.01)
  *A61F 2/848* (2013.01)
  *A61F 2/95* (2013.01)
  *A61F 2/89* (2013.01)

(56) References Cited

U.S. PATENT DOCUMENTS

| | | |
|---|---|---|
| 3,631,854 A | 1/1972 | Fryer et al. |
| 3,657,744 A | 4/1972 | Ersek |
| 3,669,586 A | 6/1972 | Kramer |
| 3,814,137 A | 6/1974 | Martinez |
| 3,818,511 A | 6/1974 | Goldberg et al. |
| 3,902,198 A | 9/1975 | Rathjen |
| 3,991,767 A | 11/1976 | Miller et al. |
| 4,096,227 A | 6/1978 | Gore |
| 4,110,392 A | 8/1978 | Yamasaki |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,229,838 A | 10/1980 | Mano |
| 4,248,924 A | 2/1981 | Okita |
| 4,330,126 A | 5/1982 | Rumble |
| 4,385,093 A | 5/1983 | Hubis |
| 4,416,028 A | 11/1983 | Eriksson et al. |
| 4,434,797 A | 3/1984 | Silander |
| 4,459,252 A | 7/1984 | MacGregor |
| 4,474,630 A | 10/1984 | Planck et al. |
| 4,478,665 A | 10/1984 | Hubis |
| 4,482,516 A | 11/1984 | Bowman et al. |
| 4,497,074 A | 2/1985 | Rey et al. |
| 4,503,569 A | 3/1985 | Dotter |
| 4,512,338 A | 4/1985 | Balko et al. |
| 4,550,447 A | 11/1985 | Seiler, Jr. et al. |
| 4,552,707 A | 11/1985 | How |
| 4,562,596 A | 1/1986 | Kornberg |
| 4,577,631 A | 3/1986 | Kreamer |
| 4,580,568 A | 4/1986 | Gianturco |
| 4,592,754 A | 6/1986 | Gupte et al. |
| 4,617,932 A | 10/1986 | Kornberg |
| 4,647,416 A | 3/1987 | Seiler, Jr. et al. |
| 4,655,769 A | 4/1987 | Zachariades |
| 4,655,771 A | 4/1987 | Wallsten |
| 4,665,906 A | 5/1987 | Jervis |
| 4,705,517 A | 11/1987 | DiPisa, Jr. |
| 4,731,073 A | 3/1988 | Robinson |
| 4,733,665 A | 3/1988 | Palmaz |
| 4,739,762 A | 4/1988 | Palmaz |
| 4,740,207 A | 4/1988 | Kreamer |
| 4,743,480 A | 5/1988 | Campbell et al. |
| 4,760,102 A | 7/1988 | Moriyama et al. |
| 4,776,337 A | 10/1988 | Palmaz |
| 4,787,899 A | 11/1988 | Lazarus |
| 4,816,028 A | 3/1989 | Kapadia et al. |
| 4,830,003 A | 5/1989 | Wolff et al. |
| 4,856,516 A | 8/1989 | Hillstead |
| 4,871,365 A | 10/1989 | Dumican |
| 4,877,661 A | 10/1989 | House et al. |
| 4,902,423 A | 2/1990 | Bacino |
| 4,932,938 A | 6/1990 | Goldberg et al. |
| 4,941,870 A | 7/1990 | Okada et al. |
| 4,955,899 A | 9/1990 | Della et al. |
| 4,957,669 A | 9/1990 | Primm |
| 4,985,296 A | 1/1991 | Mortimer, Jr. |
| 4,994,071 A | 2/1991 | MacGregor |
| 4,994,077 A | 2/1991 | Dobben |
| 5,019,090 A | 5/1991 | Pinchuk |
| 5,041,126 A | 8/1991 | Gianturco |
| 5,052,998 A | 10/1991 | Zimmon |
| 5,059,211 A | 10/1991 | Stack et al. |
| 5,064,435 A | 11/1991 | Porter |
| 5,098,625 A | 3/1992 | Huang et al. |
| 5,100,422 A | 3/1992 | Berguer et al. |
| 5,104,399 A | 4/1992 | Lazarus |
| 5,104,400 A | 4/1992 | Berguer et al. |
| 5,104,404 A | 4/1992 | Wolff |
| 5,108,424 A | 4/1992 | Hoffman, Jr. et al. |
| 5,110,527 A | 5/1992 | Harada et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,139,480 A | 8/1992 | Hickle et al. |
| 5,150,304 A | 9/1992 | Berchem et al. |
| 5,151,105 A | 9/1992 | Kwan-Gett |
| 5,152,782 A | 10/1992 | Kowligi et al. |
| 5,156,620 A | 10/1992 | Pigott |
| 5,158,548 A | 10/1992 | Lau et al. |
| 5,163,955 A | 11/1992 | Love |
| 5,167,614 A | 12/1992 | Tessmann et al. |
| 5,171,262 A | 12/1992 | MacGregor |
| 5,192,310 A | 3/1993 | Herweck et al. |
| 5,195,984 A | 3/1993 | Schatz |
| 5,197,976 A | 3/1993 | Herweck et al. |
| 5,197,978 A | 3/1993 | Hess |
| 5,201,757 A | 4/1993 | Heyn et al. |
| 5,202,352 A | 4/1993 | Okada et al. |
| 5,207,695 A | 5/1993 | Trout, III |
| 5,217,483 A | 6/1993 | Tower |
| 5,219,355 A | 6/1993 | Parodi et al. |
| 5,226,913 A | 7/1993 | Pinchuk |
| 5,234,456 A | 8/1993 | Silvestini |
| 5,250,059 A | 10/1993 | Andreas et al. |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,320,100 A | 6/1994 | Herweck et al. |
| 5,321,109 A | 6/1994 | Bosse et al. |
| 5,330,528 A | 7/1994 | Lazim |
| 5,334,164 A | 8/1994 | Guy et al. |
| 5,334,201 A | 8/1994 | Cowan |
| 5,344,426 A | 9/1994 | Lau et al. |
| 5,344,444 A | 9/1994 | Glastra |
| 5,344,451 A | 9/1994 | Dayton |
| 5,350,398 A | 9/1994 | Pavcnik |
| 5,354,310 A | 10/1994 | Garnic et al. |
| 5,354,329 A | 10/1994 | Whalen |
| 5,360,443 A | 11/1994 | Barone et al. |
| 5,365,996 A | 11/1994 | Crook |
| 5,366,504 A | 11/1994 | Andersen et al. |
| 5,370,682 A | 12/1994 | Schmitt |
| 5,370,691 A | 12/1994 | Samson |
| 5,374,473 A | 12/1994 | Knox et al. |
| 5,382,261 A | 1/1995 | Palmaz |
| 5,383,892 A | 1/1995 | Cardon et al. |
| 5,383,928 A | 1/1995 | Scott et al. |
| 5,387,235 A | 2/1995 | Chuter et al. |
| 5,389,106 A | 2/1995 | Tower et al. |
| 5,391,147 A | 2/1995 | Imran et al. |
| 5,397,345 A | 3/1995 | Lazarus |
| 5,405,377 A | 4/1995 | Cragg |
| 5,405,378 A | 4/1995 | Strecker |
| 5,405,379 A | 4/1995 | Lane |
| 5,411,550 A | 5/1995 | Herweck et al. |
| 5,415,634 A | 5/1995 | Glynn et al. |
| 5,423,851 A | 6/1995 | Samuels |
| 5,433,909 A | 7/1995 | Martakos et al. |
| 5,437,900 A | 8/1995 | Kuzowski |
| 5,441,515 A | 8/1995 | Khosravi et al. |

(56) References Cited

U.S. PATENT DOCUMENTS

| | | |
|---|---|---|
| 5,443,458 A | 8/1995 | Eury |
| 5,443,498 A | 8/1995 | Fountaine |
| 5,445,646 A | 8/1995 | Euteneuer et al. |
| 5,447,152 A | 9/1995 | Kohsai et al. |
| 5,449,373 A | 9/1995 | Pinchasik et al. |
| 5,456,713 A | 10/1995 | Chuter |
| 5,464,419 A | 11/1995 | Glastra |
| 5,464,449 A | 11/1995 | Ryan et al. |
| 5,466,509 A | 11/1995 | Kowllgl et al. |
| 5,474,824 A | 12/1995 | Martakos et al. |
| 5,476,506 A | 12/1995 | Lunn |
| 5,476,589 A | 12/1995 | Bacino |
| 5,478,330 A | 12/1995 | Imran et al. |
| 5,480,423 A | 1/1996 | Ravenscroft et al. |
| 5,489,295 A | 2/1996 | Piplani et al. |
| 5,505,887 A | 4/1996 | Zdrahala et al. |
| 5,507,769 A | 4/1996 | Marin et al. |
| 5,507,770 A | 4/1996 | Turk |
| 5,512,360 A | 4/1996 | King |
| 5,514,154 A | 5/1996 | Lau et al. |
| 5,522,880 A | 6/1996 | Barone et al. |
| 5,522,881 A | 6/1996 | Lentz |
| 5,522,883 A | 6/1996 | Slater et al. |
| 5,524,633 A | 6/1996 | Heaven et al. |
| 5,527,353 A | 6/1996 | Schmitt |
| 5,527,355 A | 6/1996 | Ahn |
| 5,529,653 A | 6/1996 | Glastra |
| 5,529,820 A | 6/1996 | Nomi et al. |
| 5,534,024 A | 7/1996 | Rogers et al. |
| 5,536,274 A | 7/1996 | Neuss |
| 5,545,135 A | 8/1996 | Iacob et al. |
| 5,549,662 A | 8/1996 | Fordenbacher |
| 5,549,663 A | 8/1996 | Cottone, Jr. |
| 5,552,100 A | 9/1996 | Shannon et al. |
| 5,554,180 A | 9/1996 | Turk |
| 5,554,181 A | 9/1996 | Das |
| 5,554,183 A | 9/1996 | Nazari |
| 5,554,185 A | 9/1996 | Block et al. |
| 5,556,414 A | 9/1996 | Turi |
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnont |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukie et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,747,128 A | 5/1998 | Campbell et al. |
| 5,749,880 A | 5/1998 | Banas et al. |
| 5,749,894 A | 5/1998 | Engleson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |

(56) References Cited

U.S. PATENT DOCUMENTS

| | | |
|---|---|---|
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Meyers et al. |
| 5,810,872 A | 9/1998 | Kanesaka et al. |
| 5,814,405 A | 9/1998 | Branca et al. |
| 5,817,102 A | 10/1998 | Liann et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Spoeistra |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | Mcintyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A | 12/1998 | Lenker et al. |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,861,027 A | 1/1999 | Trapp |
| 5,871,536 A | 2/1999 | Lazarus |
| 5,871,537 A | 2/1999 | Holman et al. |
| 5,871,538 A | 2/1999 | Dereume |
| 5,873,906 A | 2/1999 | Lau et al. |
| 5,876,432 A | 3/1999 | Lau et al. |
| 5,891,193 A | 4/1999 | Robinson et al. |
| 5,904,713 A | 5/1999 | Leschinsky |
| 5,906,619 A | 5/1999 | Olson et al. |
| 5,906,641 A | 5/1999 | Thompson et al. |
| 5,910,168 A | 6/1999 | Meyers et al. |
| 5,910,277 A | 6/1999 | Ishlno et al. |
| 5,911,754 A | 6/1999 | Kanesaka et al. |
| 5,916,264 A | 6/1999 | Von Oepen et al. |
| 5,919,204 A | 7/1999 | Lukic et al. |
| 5,922,020 A | 7/1999 | Klein et al. |
| 5,925,061 A | 7/1999 | Ogi et al. |
| 5,925,075 A | 7/1999 | Myers et al. |
| 5,931,865 A | 8/1999 | Silverman et al. |
| 5,935,667 A | 8/1999 | Calcote et al. |
| 5,939,198 A | 8/1999 | Howard, Jr. et al. |
| 5,944,750 A | 8/1999 | Tanner et al. |
| 5,948,016 A | 9/1999 | Jang |
| 5,954,729 A | 9/1999 | Bachmann et al. |
| 5,955,016 A | 9/1999 | Goldfarb |
| 5,957,973 A | 9/1999 | Quiachon et al. |
| 5,961,545 A | 10/1999 | Lentz et al. |
| 5,961,546 A | 10/1999 | Robinson et al. |
| 5,968,068 A | 10/1999 | Dehdashtian et al. |
| 5,968,090 A | 10/1999 | Ratcliff et al. |
| 5,972,023 A | 10/1999 | Tanner et al. |
| 5,972,027 A | 10/1999 | Johnson |
| 5,972,441 A | 10/1999 | Campbell et al. |
| 5,976,155 A | 11/1999 | Foreman et al. |
| 5,976,179 A | 11/1999 | Inoue |
| 5,976,192 A | 11/1999 | McIntyre et al. |
| 5,976,650 A | 11/1999 | Campbell et al. |
| 5,980,530 A | 11/1999 | Willard et al. |
| 5,980,570 A | 11/1999 | Simpson |
| 5,984,955 A | 11/1999 | Wisselink |
| 5,984,956 A | 11/1999 | Tweden et al. |
| 5,984,964 A | 11/1999 | Roberts et al. |
| 5,989,287 A | 11/1999 | Yang et al. |
| 5,993,481 A | 11/1999 | Mercade et al. |
| 5,993,489 A | 11/1999 | Lewis et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,015,432 A | 1/2000 | Rakos et al. |
| 6,017,362 A | 1/2000 | Lau |
| 6,017,364 A | 1/2000 | Lazarus |
| 6,019,778 A | 2/2000 | Wilson et al. |
| 6,019,779 A | 2/2000 | Thorud et al. |
| 6,019,787 A | 2/2000 | Richard et al. |
| 6,022,359 A | 2/2000 | Frantzen |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,640 A | 3/2000 | Corace et al. |
| 6,036,702 A | 3/2000 | Bachinski et al. |
| 6,036,723 A | 3/2000 | Anidjar et al. |
| 6,036,724 A | 3/2000 | Lentz et al. |
| 6,036,725 A | 3/2000 | Avellanet |
| 6,039,754 A | 3/2000 | Caro |
| 6,039,758 A | 3/2000 | Quiachon et al. |
| 6,042,589 A | 3/2000 | Marianne |
| 6,042,605 A | 3/2000 | Martin et al. |
| 6,042,606 A | 3/2000 | Frantzen |
| 6,045,557 A | 4/2000 | White et al. |
| 6,048,484 A | 4/2000 | House et al. |
| 6,051,020 A | 4/2000 | Goicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,060,534 A | 5/2000 | Ronan et al. |
| 6,063,114 A | 5/2000 | Nash et al. |
| 6,068,626 A | 5/2000 | Harrington et al. |
| 6,070,589 A | 6/2000 | Keith et al. |
| 6,074,341 A | 6/2000 | Anderson et al. |
| 6,075,180 A | 6/2000 | Sharber et al. |
| 6,077,296 A | 6/2000 | Shokoohi et al. |
| 6,077,297 A | 6/2000 | Robinson et al. |
| 6,077,298 A | 6/2000 | Tu et al. |
| 6,090,128 A | 7/2000 | Douglas |
| 6,093,203 A | 7/2000 | Uflacker |
| 6,096,052 A | 8/2000 | Callister et al. |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,103,172 A | 8/2000 | Newman et al. |
| 6,106,548 A | 8/2000 | Roubin et al. |
| 6,110,198 A | 8/2000 | Fogarty et al. |
| 6,113,628 A | 9/2000 | Borghi |
| 6,117,168 A | 9/2000 | Yang et al. |
| 6,123,722 A | 9/2000 | Fogarty et al. |
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,015 A | 11/2000 | Nobles |
| 6,143,016 A | 11/2000 | Bleam et al. |

(56) References Cited

U.S. PATENT DOCUMENTS

| | | |
|---|---|---|
| 6,143,021 A | 11/2000 | Staehle |
| 6,143,022 A | 11/2000 | Shull et al. |
| 6,146,389 A | 11/2000 | Geitz |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,944 A | 11/2000 | Holman et al. |
| 6,152,956 A | 11/2000 | Pierce |
| 6,156,063 A | 12/2000 | Douglas |
| 6,156,064 A | 12/2000 | Chouinard |
| 6,159,229 A | 12/2000 | Jendersee et al. |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,614 B1 | 1/2001 | Andersen et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,619 B1 | 1/2001 | Dinh et al. |
| 6,168,620 B1 | 1/2001 | Kerr |
| 6,174,326 B1 | 1/2001 | Kitaoka et al. |
| 6,183,481 B1 | 2/2001 | Lee et al. |
| 6,183,504 B1 | 2/2001 | Inoue |
| 6,187,034 B1 | 2/2001 | Frantzen |
| 6,187,036 B1 | 2/2001 | Shaolian et al. |
| 6,187,054 B1 | 2/2001 | Colone et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,203,569 B1 | 3/2001 | Wijay |
| 6,203,735 B1 | 3/2001 | Edwin et al. |
| 6,203,779 B1 | 3/2001 | Ricci et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,224,625 B1 | 5/2001 | Jayaraman |
| 6,231,562 B1 | 5/2001 | Khosravi et al. |
| 6,235,050 B1 | 5/2001 | Quiachon et al. |
| 6,235,051 B1 | 5/2001 | Murphy |
| 6,238,432 B1 | 5/2001 | Parodi |
| 6,240,616 B1 | 6/2001 | Yan |
| 6,241,759 B1 | 6/2001 | Piplani et al. |
| 6,245,097 B1 | 6/2001 | Inoue |
| 6,245,099 B1 | 6/2001 | Edwin et al. |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,136 B1 | 6/2001 | Guruwaiya et al. |
| 6,254,593 B1 | 7/2001 | Wilson |
| 6,254,632 B1 | 7/2001 | Wu et al. |
| 6,258,073 B1 | 7/2001 | Mauch |
| 6,258,114 B1 | 7/2001 | Konya et al. |
| 6,258,116 B1 | 7/2001 | Hojeibane |
| 6,261,316 B1 | 7/2001 | Shaolian et al. |
| 6,261,317 B1 | 7/2001 | Inoue |
| 6,264,662 B1 | 7/2001 | Lauterjung |
| 6,264,684 B1 | 7/2001 | Banas et al. |
| 6,267,783 B1 | 7/2001 | Letendre et al. |
| 6,267,834 B1 | 7/2001 | Shannon et al. |
| 6,270,524 B1 | 7/2001 | Kim |
| 6,270,525 B1 | 7/2001 | Letendre et al. |
| 6,270,707 B1 | 8/2001 | Hon et al. |
| 6,273,909 B1 | 8/2001 | Kugler et al. |
| 6,273,910 B1 | 8/2001 | Limon |
| 6,273,911 B1 | 8/2001 | Cox et al. |
| 6,280,457 B1 | 8/2001 | Wallace et al. |
| 6,280,466 B1 | 8/2001 | Kugler et al. |
| 6,280,467 B1 | 8/2001 | Leonhardt et al. |
| 6,283,991 B1 | 9/2001 | Cox et al. |
| 6,287,315 B1 | 9/2001 | Wijeratne et al. |
| 6,287,329 B1 | 9/2001 | Duarig et al. |
| 6,287,330 B1 | 9/2001 | Johansson et al. |
| 6,287,335 B1 | 9/2001 | Drasler et al. |
| 6,287,336 B1 | 9/2001 | Globerman et al. |
| 6,290,728 B1 | 9/2001 | Phelps et al. |
| 6,293,966 B1 | 9/2001 | Frantzen |
| 6,293,968 B1 | 9/2001 | Taheri |
| 6,293,969 B1 | 9/2001 | Chuter |
| 6,296,661 B1 | 10/2001 | Davila et al. |
| 6,302,891 B1 | 10/2001 | Nadal |
| 6,302,905 B1 | 10/2001 | Goldstein et al. |
| 6,302,906 B1 | 10/2001 | Goicoechea et al. |
| 6,302,908 B1 | 10/2001 | Parodi |
| 6,303,100 B1 | 10/2001 | Ricci et al. |
| 6,306,141 B1 | 10/2001 | Jervis |
| 6,306,145 B1 | 10/2001 | Laschinsky |
| 6,306,164 B1 | 10/2001 | Kujawski |
| 6,306,165 B1 | 10/2001 | Patnaik et al. |
| 6,312,458 B1 | 11/2001 | Golds |
| 6,312,460 B2 | 11/2001 | Drasler et al. |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,325,824 B2 | 12/2001 | Limon |
| 6,325,825 B1 | 12/2001 | Kula et al. |
| 6,328,762 B1 | 12/2001 | Anderson et al. |
| 6,331,186 B1 | 12/2001 | Wang et al. |
| 6,331,188 B1 | 12/2001 | Lau et al. |
| 6,331,190 B1 | 12/2001 | Shokoohi et al. |
| 6,331,191 B1 | 12/2001 | Chobotov |
| 6,334,869 B1 | 1/2002 | Leonhardt et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,344,055 B1 | 2/2002 | Shukov |
| 6,346,118 B1 | 2/2002 | Baker et al. |
| 6,346,119 B1 | 2/2002 | Kuwahara et al. |
| 6,348,065 B1 | 2/2002 | Brown et al. |
| 6,350,277 B1 | 2/2002 | Kocur |
| 6,352,553 B1 | 3/2002 | Van der Burg et al. |
| 6,352,561 B1 | 3/2002 | Leopold et al. |
| 6,355,055 B1 | 3/2002 | Waksman et al. |
| 6,355,056 B1 | 3/2002 | Pnheiro |
| 6,355,060 B1 | 3/2002 | Lenker et al. |
| 6,355,063 B1 | 3/2002 | Calcote |
| 6,357,104 B1 | 3/2002 | Myers |
| 6,358,276 B1 | 3/2002 | Edwin et al. |
| 6,358,284 B1 | 3/2002 | Fearnot et al. |
| 6,361,637 B2 | 3/2002 | Martin et al. |
| 6,363,938 B2 | 4/2002 | Saadat |
| 6,364,856 B1 | 4/2002 | Ding et al. |
| 6,364,904 B1 | 4/2002 | Smith |
| 6,368,346 B1 | 4/2002 | Jadhav |
| 6,368,347 B1 | 4/2002 | Maini et al. |
| 6,368,355 B1 | 4/2002 | Uflacker |
| 6,371,979 B1 | 4/2002 | Beyar et al. |

(56) References Cited

U.S. PATENT DOCUMENTS

| | | |
|---|---|---|
| 6,372,136 B1 | 4/2002 | Nakatsuka |
| 6,375,787 B1 | 4/2002 | Lukic |
| 6,379,381 B1 | 4/2002 | Hossainy et al. |
| 6,379,382 B1 | 4/2002 | Yang |
| 6,379,392 B1 | 4/2002 | Walak |
| 6,383,213 B2 | 5/2002 | Wilson et al. |
| 6,383,214 B1 | 5/2002 | Banas et al. |
| 6,387,119 B2 | 5/2002 | Wolf et al. |
| 6,387,124 B1 | 5/2002 | Buscemi et al. |
| 6,391,050 B1 | 5/2002 | Broome |
| 6,391,052 B2 | 5/2002 | Buirge et al. |
| 6,395,019 B2 * | 5/2002 | Chobotov .............. A61F 2/07 623/1.13 |
| 6,395,022 B1 | 5/2002 | Piplani et al. |
| 6,395,208 B1 | 5/2002 | Herweck et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,749 B1 | 6/2002 | Maynard |
| 6,409,750 B1 | 6/2002 | Hyodoh |
| 6,409,754 B1 | 6/2002 | Smith et al. |
| 6,409,756 B1 | 6/2002 | Murphy |
| 6,409,757 B1 | 6/2002 | Trout et al. |
| 6,409,761 B1 | 6/2002 | Jang |
| 6,413,269 B1 | 7/2002 | Bui et al. |
| 6,416,535 B1 | 7/2002 | Lazarus |
| 6,416,536 B1 | 7/2002 | Yee |
| 6,416,537 B1 | 7/2002 | Martakos et al. |
| 6,416,538 B1 | 7/2002 | Ley et al. |
| 6,416,539 B1 | 7/2002 | Hassdenteufel |
| 6,416,542 B1 | 7/2002 | Marcade et al. |
| 6,419,701 B1 | 7/2002 | Cook et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,855 B2 | 7/2002 | Tomonto |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,566 B1 | 8/2002 | Holt |
| 6,428,567 B2 | 8/2002 | Wilson et al. |
| 6,428,569 B1 | 8/2002 | Brown |
| 6,428,570 B1 | 8/2002 | Globerman |
| 6,428,571 B1 | 8/2002 | Lentz et al. |
| 6,432,129 B2 | 8/2002 | DiCaprio |
| 6,432,131 B1 | 8/2002 | Ravenscroft |
| 6,432,132 B1 | 8/2002 | Cottone et al. |
| 6,436,104 B2 | 8/2002 | Hoieibane |
| 6,436,133 B1 | 8/2002 | Furst et al. |
| 6,436,134 B2 | 8/2002 | Richter et al. |
| 6,436,135 B1 | 8/2002 | Goldfarb |
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,051 B2 | 9/2002 | Drasler et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazoglou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B2 | 8/2003 | Wallace et al. |
| 6,602,280 B2 | 8/2003 | Chobotov |
| 6,602,283 B2 | 8/2003 | Doran et al. |

(56) References Cited

U.S. PATENT DOCUMENTS

| | | | |
|---|---|---|---|
| 6,605,110 B2 | 8/2003 | Harrison | |
| 6,607,551 B1 | 8/2003 | Sullivan et al. | |
| 6,613,082 B2 | 9/2003 | Yang | |
| 6,613,083 B2 | 9/2003 | Alt | |
| 6,613,084 B2 | 9/2003 | Yang | |
| 6,620,190 B1 | 9/2003 | Colone | |
| 6,626,938 B1 | 9/2003 | Butaric et al. | |
| 6,635,079 B2 | 10/2003 | Unsworth et al. | |
| 6,645,240 B2 | 11/2003 | Yee | |
| 6,652,554 B1 | 11/2003 | Wholey et al. | |
| 6,652,570 B2 | 11/2003 | Smith et al. | |
| 6,652,573 B2 | 11/2003 | Oepen | |
| 6,652,575 B2 | 11/2003 | Wang | |
| 6,652,580 B1 | 11/2003 | Chutter | |
| 6,656,215 B1 | 12/2003 | Yanez et al. | |
| 6,656,506 B1 | 12/2003 | Wu et al. | |
| 6,660,030 B2 | 12/2003 | Shaolian et al. | |
| 6,663,662 B2 | 12/2003 | Pacetti et al. | |
| 6,663,663 B2 | 12/2003 | Kim et al. | |
| 6,663,664 B1 | 12/2003 | Pacitti | |
| 6,663,665 B2 | 12/2003 | Shaolian et al. | |
| 6,663,667 B2 | 12/2003 | Dehdashtian et al. | |
| 6,669,720 B1 | 12/2003 | Pierce | |
| 6,669,723 B2 | 12/2003 | Killion et al. | |
| 6,669,724 B2 | 12/2003 | Park et al. | |
| 6,673,102 B1 | 1/2004 | Vonesh et al. | |
| 6,673,103 B1 | 1/2004 | Golds et al. | |
| 6,673,106 B2 | 1/2004 | Mitelberg et al. | |
| 6,673,107 B1 | 1/2004 | Brandt et al. | |
| 6,676,667 B2 | 1/2004 | Mareiro et al. | |
| 6,676,695 B2 | 1/2004 | Solem | |
| 6,679,911 B2 | 1/2004 | Burgermeister | |
| 6,685,736 B1 | 2/2004 | White et al. | |
| 6,689,158 B1 | 2/2004 | White et al. | |
| 6,689,159 B2 | 2/2004 | Hartigan et al. | |
| 6,692,523 B2 | 2/2004 | Holman et al. | |
| 6,694,983 B2 | 2/2004 | Hall et al. | |
| 6,695,833 B1 | 2/2004 | Frantzen | |
| 6,695,875 B2 | 2/2004 | Stelter et al. | |
| 6,695,877 B2 | 2/2004 | Brucker et al. | |
| 6,696,666 B2 | 2/2004 | Merdan et al. | |
| 6,699,274 B2 | 3/2004 | Stinson | |
| 6,699,277 B1 | 3/2004 | Freidberg et al. | |
| 6,702,847 B2 | 3/2004 | DiCarlo | |
| 6,702,849 B1 | 3/2004 | Dutta et al. | |
| 6,706,064 B1 | 3/2004 | Anson | |
| 6,709,449 B2 | 3/2004 | Camrud et al. | |
| 6,709,455 B1 | 3/2004 | Chouinard | |
| 6,712,827 B2 | 3/2004 | Ellis et al. | |
| 6,716,238 B2 | 4/2004 | Elliott | |
| 6,716,239 B2 | 4/2004 | Sowinski | |
| 6,719,783 B2 | 4/2004 | Lentz et al. | |
| 6,726,712 B1 | 4/2004 | Raeder-Devens | |
| 6,730,119 B1 | 5/2004 | Smalling | |
| 6,733,521 B2 | 5/2004 | Chobotov et al. | |
| 6,736,839 B2 | 5/2004 | Cummings | |
| 6,740,111 B1 | 5/2004 | Lauterjung | |
| 6,740,114 B2 | 5/2004 | Burgermeister | |
| 6,740,115 B2 | 5/2004 | Lombardi | |
| 6,743,210 B2 | 6/2004 | Hart et al. | |
| 6,743,511 B2 | 6/2004 | Dittrich et al. | |
| 6,746,890 B2 | 6/2004 | Gupta | |
| 6,752,589 B2 | 6/2004 | Kocur et al. | |
| 6,755,855 B2 | 6/2004 | Yurek et al. | |
| 6,758,858 B2 | 7/2004 | McCrea et al. | |
| 6,761,733 B2 | 7/2004 | Chobotov et al. | |
| 6,770,086 B1 | 8/2004 | Girton et al. | |
| 6,770,087 B2 | 8/2004 | Layne et al. | |
| 6,773,453 B2 | 8/2004 | Ravenscroft | |
| 6,773,457 B2 | 8/2004 | Gellman et al. | |
| 6,776,604 B1 | 8/2004 | Chobotov et al. | |
| 6,776,793 B2 | 8/2004 | Brown et al. | |
| 6,786,920 B2 | 8/2004 | Shannon et al. | |
| 6,790,227 B2 | 8/2004 | Burgermeister | |
| 6,790,230 B2 | 8/2004 | Beyersdorf et al. | |
| 6,793,672 B2 | 8/2004 | Khosravi et al. | |
| 6,796,999 B2 | 8/2004 | Pinchasik | |
| 6,802,849 B2 | 10/2004 | Siaeser et al. | |
| 6,802,856 B2 | 10/2004 | Wilson | |
| 6,802,859 B1 | 10/2004 | Pazienza et al. | |
| 6,814,753 B2 | 11/2004 | Schmitt | |
| 6,818,013 B2 | 11/2004 | Mitelberg et al. | |
| 6,821,292 B2 | 11/2004 | Pazienza et al. | |
| 6,824,558 B2 | 11/2004 | Parodi | |
| 6,827,726 B2 | 12/2004 | Parodi | |
| 6,827,731 B2 | 12/2004 | Annstrong et al. | |
| 6,827,735 B2 | 12/2004 | Greenbeg | |
| 6,827,737 B2 | 12/2004 | Hill et al. | |
| 6,833,004 B2 | 12/2004 | Ishil et al. | |
| 6,841,213 B2 | 1/2005 | Parsonage et al. | |
| 6,843,802 B1 | 1/2005 | Villalobos et al. | |
| 6,849,086 B2 | 2/2005 | Cragg | |
| 6,858,035 B2 | 2/2005 | Whayne | |
| 6,860,900 B2 | 3/2005 | Clerc et al. | |
| 6,863,685 B2 | 3/2005 | Davila et al. | |
| 6,866,805 B2 | 3/2005 | Hong et al. | |
| 6,869,443 B2 | 3/2005 | Buscemi et al. | |
| 6,878,160 B2 | 4/2005 | Gilligan et al. | |
| 6,878,161 B2 | 4/2005 | Lenker | |
| 6,884,260 B2 | 4/2005 | Kugler et al. | |
| 6,899,728 B1 | 5/2005 | Philips et al. | |
| 6,918,925 B2 | 7/2005 | Tehrani | |
| 6,918,927 B2 | 7/2005 | Bates et al. | |
| 6,923,827 B2 | 8/2005 | Campbell et al. | |
| 6,926,732 B2 | 8/2005 | Derus et al. | |
| 6,929,659 B2 | 8/2005 | Pinchuk | |
| 6,929,709 B2 * | 8/2005 | Smith | A61F 2/07 156/187 |
| 6,939,370 B2 | 9/2005 | Hartley et al. | |
| 6,939,374 B2 | 9/2005 | Banik et al. | |
| 6,942,689 B2 | 9/2005 | Majercak | |
| 6,945,989 B1 | 9/2005 | Rourke et al. | |
| 6,945,992 B2 | 9/2005 | Goodson et al. | |
| 6,949,120 B2 | 9/2005 | Kveen et al. | |
| 6,962,602 B2 | 11/2005 | Vardi et al. | |
| 6,962,603 B1 | 11/2005 | Brown | |
| 6,964,677 B2 | 11/2005 | Osypka | |
| 6,974,471 B2 | 12/2005 | Van Schie et al. | |
| 6,974,472 B2 | 12/2005 | Hong et al. | |
| 6,981,982 B2 | 1/2006 | Armstrong et al. | |
| 6,989,026 B2 | 1/2006 | Richter et al. | |
| 6,994,722 B2 | 2/2006 | DiCarlo | |
| 6,997,945 B2 | 2/2006 | Germain | |
| 6,998,060 B2 | 2/2006 | Tomonto | |
| 7,001,407 B2 | 2/2006 | Hansen et al. | |
| 7,001,419 B2 | 2/2006 | DiCaprio et al. | |
| 7,001,431 B2 | 2/2006 | Bao et al. | |
| 7,011,673 B2 | 4/2006 | Fischell et al. | |
| 7,011,674 B2 | 4/2006 | Brenneman | |
| 7,022,132 B2 | 4/2006 | Kocur | |
| 7,022,135 B2 | 4/2006 | Zilla et al. | |
| 7,033,389 B2 | 4/2006 | Sherry | |
| 7,056,325 B1 | 6/2006 | Makower | |
| 7,056,336 B2 | 6/2006 | Armstrong et al. | |
| 7,056,412 B2 | 6/2006 | Henderson | |
| 7,066,951 B2 | 6/2006 | Chobotov | |
| 7,073,504 B2 | 7/2006 | Callister et al. | |
| 7,081,129 B2 | 7/2006 | Chobotov | |
| 7,081,132 B2 | 7/2006 | Cook | |
| 7,083,642 B2 | 8/2006 | Sirhan et al. | |
| 7,090,693 B1 | 8/2006 | Chobotov et al. | |
| 7,094,255 B2 | 8/2006 | Penn et al. | |
| 7,108,715 B2 | 9/2006 | Brown et al. | |
| 7,115,140 B2 | 10/2006 | Stoltze et al. | |
| 7,125,464 B2 | 10/2006 | Chobotov et al. | |
| 7,128,754 B2 | 10/2006 | Bolduc | |
| 7,128,755 B2 | 10/2006 | Su et al. | |
| 7,147,455 B2 | 12/2006 | Chobotov et al. | |
| 7,147,660 B2 | 12/2006 | Chobotov et al. | |
| 7,147,661 B2 | 12/2006 | Chobotov et al. | |
| 7,150,758 B2 | 12/2006 | Kari et al. | |
| 7,160,318 B2 | 1/2007 | Greenberg et al. | |
| 7,163,553 B2 | 1/2007 | Limon | |
| 7,166,125 B1 | 1/2007 | Baker et al. | |

(56) References Cited

U.S. PATENT DOCUMENTS

| | | |
|---|---|---|
| 7,175,651 B2 | 2/2007 | Kerr |
| 7,175,652 B2 | 2/2007 | Cook et al. |
| 7,189,256 B2 | 3/2007 | Smith |
| 7,192,441 B2 | 3/2007 | Sherry |
| 7,223,280 B2 | 3/2007 | Anson et al. |
| 7,226,474 B2 | 6/2007 | Iancea et al. |
| 7,229,470 B2 | 6/2007 | Brian et al. |
| 7,232,459 B2 | 6/2007 | Greenberg |
| 7,243,408 B2 | 7/2007 | Vietmeier |
| 7,244,242 B2 | 7/2007 | Freyman |
| 7,273,494 B2 | 9/2007 | Rolando et al. |
| 7,284,399 B1 | 10/2007 | Sisco |
| 7,294,147 B2 | 11/2007 | Hartley |
| 7,314,484 B2 | 1/2008 | Deem et al. |
| 7,318,835 B2 | 1/2008 | Berra |
| 7,338,518 B2 | 3/2008 | Chobotov |
| 7,351,256 B2 | 4/2008 | Hojeibane et al. |
| 7,425,219 B2 | 9/2008 | Quadri |
| 7,452,374 B2 | 10/2008 | Hain et al. |
| 7,465,270 B2 | 12/2008 | Li |
| 7,476,245 B2 | 1/2009 | Abbate |
| 7,485,138 B2 | 2/2009 | Fearnot et al. |
| 7,491,230 B2 | 2/2009 | Holman et al. |
| 7,491,234 B2 | 2/2009 | Palasis et al. |
| 7,500,988 B1 | 3/2009 | Butaric et al. |
| 7,510,571 B2 | 3/2009 | Spiridiglozzi et al. |
| 7,520,890 B2 | 4/2009 | Phillips |
| 7,520,895 B2 | 4/2009 | Douglas et al. |
| 7,530,988 B2 | 5/2009 | Evans et al. |
| 7,550,004 B2 | 6/2009 | Bahaler et al. |
| 7,550,005 B2 | 6/2009 | Bates et al. |
| 7,556,645 B2 | 7/2009 | Lashinski et al. |
| 7,591,843 B1 | 9/2009 | Escano |
| 7,597,710 B2 | 10/2009 | Obermiller |
| 7,604,661 B2 | 10/2009 | Pavnick et al. |
| 7,628,803 B2 | 12/2009 | Pavnick et al. |
| 7,766,954 B2 | 8/2010 | Chobotov et al. |
| 7,976,575 B2 | 7/2011 | Hartley |
| 8,025,693 B2 | 9/2011 | Quigley |
| 8,043,356 B2 | 10/2011 | Kolbel et al. |
| 8,066,755 B2 | 11/2011 | Zacharias et al. |
| 8,252,036 B2 | 8/2012 | Cartledge et al. |
| 8,535,370 B1 | 9/2013 | Eckert et al. |
| 8,784,477 B2 | 7/2014 | Bregulla et al. |
| 9,060,852 B2 | 6/2015 | Grewe et al. |
| 2001/0014794 A1 | 8/2001 | Moll |
| 2001/0019659 A1 | 9/2001 | Hirai |
| 2001/0029349 A1 | 10/2001 | Leschinsky |
| 2001/0039445 A1 | 11/2001 | Hall et al. |
| 2001/0041928 A1 | 11/2001 | Pavenik et al. |
| 2001/0044652 A1 | 11/2001 | Moore |
| 2001/0049534 A1 | 12/2001 | Lachat |
| 2002/0002400 A1 | 1/2002 | Drasler et al. |
| 2002/0007193 A1 | 1/2002 | Tanner et al. |
| 2002/0011684 A1 | 1/2002 | Bahar et al. |
| 2002/0016626 A1 | 2/2002 | DiMatteo et al. |
| 2002/0029051 A1 | 3/2002 | Callister et al. |
| 2002/0032408 A1 | 3/2002 | Parker et al. |
| 2002/0035395 A1 | 3/2002 | Sigimoto |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052644 A1 | 5/2002 | Shaolin et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0076542 A1 | 6/2002 | Kramer et al. |
| 2002/0077692 A1 | 6/2002 | Besselink |
| 2002/0082680 A1 | 6/2002 | Stanley et al. |
| 2002/0082682 A1 | 6/2002 | Barclay et al. |
| 2002/0082685 A1 | 6/2002 | Sirhan et al. |
| 2002/0095208 A1 | 7/2002 | Gregorich et al. |
| 2002/0096252 A1 | 7/2002 | Lukic |
| 2002/0107561 A1 | 8/2002 | Pinheiro |
| 2002/0116050 A1 | 8/2002 | Kocur |
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0151956 A1 | 10/2002 | Chobotov et al. |
| 2002/0156522 A1 | 10/2002 | Ryan et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188344 A1 | 12/2002 | Bolea et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1 | 1/2003 | Chobotov et al. |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0033001 A1 | 2/2003 | Igaki |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0074050 A1 | 4/2003 | Kerr |
| 2003/0083736 A1 | 5/2003 | Brown et al. |
| 2003/0088305 A1 | 5/2003 | Van Schie et al. |
| 2003/0097170 A1 | 5/2003 | Friedrich et al. |
| 2003/0116260 A1 | 6/2003 | Chobotov et al. |
| 2003/0120263 A1* | 6/2003 | Ouriel ............... A61B 17/221 606/1 |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridiglozzi et al. |
| 2003/0204236 A1 | 10/2003 | Letort |
| 2003/0204244 A1 | 10/2003 | Stiger |
| 2003/0212449 A1 | 11/2003 | Cox |
| 2003/0220683 A1 | 11/2003 | Minasian |
| 2003/0225453 A1 | 12/2003 | Murch |
| 2004/0024446 A1 | 2/2004 | Smith |
| 2004/0034407 A1 | 2/2004 | Sherry |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098091 A1 | 5/2004 | Erbel et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1 | 7/2004 | Chobotov et al. |
| 2004/0148008 A1 | 7/2004 | Goodson et al. |
| 2004/0162607 A1 | 8/2004 | Masroor |
| 2004/0167614 A1 | 8/2004 | Anson |
| 2004/0167619 A1 | 8/2004 | Case et al. |
| 2004/0176836 A1 | 9/2004 | Chobotov |
| 2004/0186558 A1 | 9/2004 | Pavnick et al. |

(56) References Cited

U.S. PATENT DOCUMENTS

| | | |
|---|---|---|
| 2004/0210304 A1 | 10/2004 | Seguin et al. |
| 2004/0215213 A1 | 10/2004 | Dolan |
| 2004/0220655 A1 | 11/2004 | Swanson et al. |
| 2004/0220664 A1 | 11/2004 | Chobotov |
| 2004/0254625 A1 | 12/2004 | Stephens |
| 2005/0033406 A1 | 2/2005 | Barnhart et al. |
| 2005/0049674 A1 | 3/2005 | Berra et al. |
| 2005/0049691 A1 | 3/2005 | Mercile et al. |
| 2005/0058920 A1 | 3/2005 | Tokarski et al. |
| 2005/0075715 A1 | 4/2005 | Borges et al. |
| 2005/0090804 A1 | 4/2005 | Chobotov et al. |
| 2005/0090901 A1 | 4/2005 | Studer |
| 2005/0154443 A1 | 7/2005 | Linder et al. |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0178732 A1 | 8/2005 | Chobotov et al. |
| 2005/0222669 A1 | 10/2005 | Purdy |
| 2005/0228484 A1 | 10/2005 | Stephens et al. |
| 2006/0009833 A1 | 1/2006 | Chobotov et al. |
| 2006/0020319 A1 | 1/2006 | Kim |
| 2006/0030921 A1 | 2/2006 | Berra |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0161244 A1 | 7/2006 | Seguin |
| 2006/0161245 A1 | 7/2006 | Rakos et al. |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbeferize |
| 2007/0100427 A1 | 5/2007 | Perouse |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Lashinski et al. |
| 2008/0027529 A1 | 1/2008 | Hartley et al. |
| 2008/0039926 A1 | 2/2008 | Majercak et al. |
| 2008/0051705 A1 | 2/2008 | Von Oepen et al. |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0132995 A1 | 6/2008 | Burgermeister et al. |
| 2008/0172119 A1 | 7/2008 | Yamasaki et al. |
| 2008/0115678 A1 | 9/2008 | Clarke et al. |
| 2008/0228255 A1 | 9/2008 | Rust |
| 2008/0255652 A1 | 10/2008 | Thomas et al. |
| 2009/0005854 A1 | 1/2009 | Huang et al. |
| 2009/0036971 A1 | 2/2009 | Humphrey et al. |
| 2009/0082841 A1 | 3/2009 | Zacharias et al. |
| 2009/0082842 A1 | 3/2009 | Glynn |
| 2009/0082845 A1 | 3/2009 | Chobotov et al. |
| 2009/0082846 A1 | 3/2009 | Chobotov et al. |
| 2009/0082847 A1 | 3/2009 | Zacharias et al. |
| 2009/0092844 A1 | 3/2009 | Zacharias et al. |
| 2009/0099649 A1 | 4/2009 | Chobotov et al. |
| 2009/0042796 A1 | 5/2009 | Wallach et al. |
| 2009/0125095 A1 | 5/2009 | Bui et al. |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182406 A1 | 7/2009 | Blaeser et al. |
| 2009/0198267 A1 | 8/2009 | Evans et al. |
| 2009/0287145 A1 | 11/2009 | Cragg |
| 2010/0114290 A1 | 5/2010 | Rassmussen et al. |
| 2010/0161028 A1 | 6/2010 | Chuter et al. |
| 2010/0211052 A1 | 8/2010 | Brown et al. |
| 2010/0249908 A1 | 9/2010 | Chau et al. |
| 2010/0286760 A1 | 11/2010 | Beach et al. |
| 2010/0305686 A1 | 12/2010 | Cragg |
| 2010/0331958 A1 | 12/2010 | Chobotov et al. |
| 2011/0130819 A1 | 6/2011 | Cragg |
| 2011/0130820 A1 | 6/2011 | Cragg |
| 2011/0130824 A1 | 6/2011 | Cragg |
| 2011/0130825 A1 | 6/2011 | Cragg |
| 2011/0130826 A1 | 6/2011 | Cragg |
| 2011/0218609 A1 | 9/2011 | Chobotov et al. |
| 2011/0238160 A1 | 9/2011 | Molony |
| 2011/0295356 A1 | 12/2011 | Abunassar |
| 2012/0016457 A1 | 1/2012 | Chobotov et al. |
| 2012/0041543 A1 | 2/2012 | Huang et al. |
| 2012/0130469 A1 | 5/2012 | Cragg |
| 2012/0191174 A1 | 7/2012 | Vinluan et al. |
| 2013/0090715 A1 | 4/2013 | Chobotov et al. |
| 2013/0268044 A1 | 10/2013 | Parsons et al. |
| 2013/0268048 A1 | 10/2013 | Watson et al. |

FOREIGN PATENT DOCUMENTS

| | | |
|---|---|---|
| EP | 0646365 | 4/1995 |
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0878175 | 11/1998 |
| EP | 0943302 | 9/1999 |
| EP | 0997115 | 5/2000 |
| EP | 0480667 | 4/2001 |
| EP | 1093772 | 4/2001 |
| EP | 1138280 | 10/2001 |
| EP | A 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| EP | 1 611 867 | 1/2006 |
| EP | 1683541 | 7/2006 |
| EP | 2 158 880 | 3/2010 |
| EP | 1360967 | 11/2013 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |
| SU | 1768154 | 10/1992 |
| SU | 1812980 | 4/1993 |
| WO | WO 91/000792 | 1/1991 |
| WO | WO 92/022604 | 12/1992 |
| WO | WO 93/013824 | 7/1993 |
| WO | WO 93/019804 | 10/1993 |
| WO | WO 94/003127 | 2/1994 |
| WO | WO 95/01761 | 1/1995 |
| WO | WO 95/003754 | 2/1995 |

(56) References Cited

FOREIGN PATENT DOCUMENTS

| WO | WO 95/005132 | 2/1995 |
|---|---|---|
| WO | WO 95/009586 | 4/1995 |
| WO | WO 96/014095 | 5/1996 |
| WO | WO 96/14808 | 5/1996 |
| WO | WO 97/03624 | 2/1997 |
| WO | WO 97/007751 | 3/1997 |
| WO | WO 97/29716 | 8/1997 |
| WO | WO 97/048350 | 12/1997 |
| WO | WO 98/006355 | 2/1998 |
| WO | WO 98/038947 | 9/1998 |
| WO | WO 98/041167 | 9/1998 |
| WO | WO 98/044870 | 10/1998 |
| WO | WO 98/044873 | 10/1998 |
| WO | WO 99/000073 | 1/1999 |
| WO | WO 99/026559 | 6/1999 |
| WO | WO 99/038455 | 8/1999 |
| WO | WO 99/043378 | 9/1999 |
| WO | WO 99/043379 | 9/1999 |
| WO | WO 00/010487 | 3/2000 |
| WO | WO 00/13613 | 3/2000 |
| WO | WO 00/042947 | 7/2000 |
| WO | WO 00/042948 | 7/2000 |
| WO | WO 00/044808 | 8/2000 |
| WO | WO 00/051522 | 9/2000 |
| WO | WO 00/67675 | 11/2000 |
| WO | WO 00/071179 | 11/2000 |
| WO | WO 01/05331 | 1/2001 |
| WO | WO 01/008599 | 2/2001 |
| WO | WO 01/015633 | 3/2001 |
| WO | WO 01/021108 | 3/2001 |
| WO | WO 01/030270 | 5/2001 |
| WO | WO 01/041675 | 6/2001 |
| WO | WO 01/056500 | 8/2001 |
| WO | WO 01/056504 | 8/2001 |
| WO | WO 01/058384 | 8/2001 |
| WO | WO 01/58387 | 8/2001 |
| WO | WO 01/066037 | 9/2001 |
| WO | WO 01/067993 | 9/2001 |
| WO | WO 01/074270 | 10/2001 |
| WO | WO 01/076509 | 10/2001 |
| WO | WO 01/082836 | 11/2001 |
| WO | WO 02/036332 | 5/2002 |
| WO | WO 02/041804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/053288 | 7/2003 |
| WO | WO 03/094795 | 11/2003 |
| WO | WO 03/094799 | 11/2003 |
| WO | WO 04/002370 | 1/2004 |
| WO | WO 04/002371 | 1/2004 |
| WO | WO 04/017866 | 3/2004 |
| WO | WO 04/078065 | 9/2004 |
| WO | WO 05/037076 | 4/2005 |
| WO | WO 05/086942 | 9/2005 |
| WO | WO 06/107562 | 10/2006 |
| WO | WO 09/042796 | 4/2009 |
| WO | WO 09/086200 | 7/2009 |
| WO | WO 11/100367 | 8/2011 |
| WO | WO 12/068175 | 8/2012 |

OTHER PUBLICATIONS

Office Action dated Dec. 7, 2011 in U.S. Appl. No. 11/861,756, filed Sep. 26, 2007 and published as: US2009/0082842 on Mar. 26, 2009.
Office Action Response dated Oct. 21, 2011 in U.S. Appl. No. 11/861,756, filed Sep. 26, 2007 and published as: US2009/0082842 on Mar. 26, 2009.
Office Action dated Nov. 28, 2011 in U.S. Appl. No. 12/747,499, filed Sep. 7, 2010 and published as: US2010/0331958 on: Dec. 30, 2010.
Office Action dated Jul. 13, 2017 in U.S. Appl. No. 14/631,818, filed Feb. 25, 2015 and published as: US-2015/0164667 on: Jun. 18, 2015.
International Search Report and Written Opinion dated Jul. 18, 2013 for International Application No. PCT/US2013/034654, filed on Mar. 29, 2013 and published as WO 2013/151896 on Oct. 10, 2013.
International Search Report and Written Opinion dated Jul. 18, 2013 for International Application No. PCT/US2013/034787, filed on Apr. 1, 2013 and published as WO 2013/151924 on Oct. 10, 2013.
Office Action dated Sep. 18, 2013 in U.S. Appl. No. 11/861,828, filed Sep. 26, 2007 and published as 2009-0082846 on Mar. 26, 2009.
Extended European Search Report dated Apr. 5, 2013 in European Application No. EP 08849544 filed: Nov. 13, 2008.
Invitation to Pay Additional Fees and Partial Search Report dated Apr. 25, 2013 for International Application No. PCT/US2011/060873 filed on Nov. 15, 2011 and published as WO/2012/068175 on Aug. 2, 2012.
International Search Report and Written Opinion dated Jun. 12, 2012 for International Application No. PCT/US2011/060873 filed on Nov. 15, 2011 and published as WO/2012/068175 on Aug. 2, 2012.
Final Office Action dated Dec. 1, 2016 in U.S. Appl. No. 14/615,337, filed Feb. 5, 2015 and published as: 2015-0157479 on Jun. 11, 2015.
Extended European Search Report dated Dec. 17, 2012 in European Application No. EP 08835032 filed: Oct. 3, 2008.
Office Action Response dated Oct. 24, 2012 in U.S. Appl. No. 11/861,739, filed Sep. 26, 2007 and published as: US2009/0082841 on Mar. 26, 2009.
Office Action dated Apr. 27, 2012 in U.S. Appl. No. 11/861,739, filed Sep. 26, 2007 and published as: US2009/0082841 on Mar. 26, 2009.
Office Action dated Jun. 7, 2012 in U.S. Appl. No. 11/861,756, filed Sep. 26, 2007 and published as: US2009/0082842 on Mar. 26, 2009.
Office Action dated Apr. 11, 2012 in U.S. Appl. No. 11/861,756, filed Sep. 26, 2007 and published as: US2009/0082842 on Mar. 26, 2009.
Office Action dated Jan. 30, 2013 in U.S. Appl. No. 12/747,499, filed Sep. 7, 2010 and published as: US2010/0331958 on: Dec. 30, 2010.
Office Action Response dated Dec. 11, 2012 in U.S. Appl. No. 12/747,499, filed Sep. 7, 2010 and published as: US2010/0331958 on: Dec. 30, 2010.
Office Action dated Jun. 18, 2012 in U.S. Appl. No. 12/747,499, filed Sep. 7, 2010 and published as: US2010/0331958 on: Dec. 30, 2010.
Office Action Response dated May 17, 2012 in U.S. Appl. No. 12/747,499, filed Sep. 7, 2010 and published as: US2010/0331958 on: Dec. 30, 2010.
Office Action dated Mar. 13, 2012 in U.S. Appl. No. 11/861,731, filed Sep. 26, 2007 and published as: US2009/0082847 on Mar. 26, 2009.
International Preliminary Report on Patentability dated Jul. 1, 2010 for International Application No. PCT/US2008/087831 filed on Dec. 19, 2008 and published as WO/2009/086200 on Jul. 9, 2009.
International Search Report and Written Opinion dated May 28, 2009 for International Application No. PCT/US2008/087831 filed on Dec. 19, 2008 and published as WO/2009/086200 on Jul. 9, 2009.
Office Action Response dated Jul. 15, 2011 in U.S. Appl. No. 11/861,739, filed Sep. 26, 2007 and published as: US2009/0082841 on Mar. 26, 2009.
Office Action dated Mar. 15, 2011 in U.S. Appl. No. 11/861,739, filed Sep. 26, 2007 and published as: US2009/0082841 on Mar. 26, 2009.
Office Action Response dated Jan. 26, 2011 in U.S. Appl. No. 11/861,739, filed Sep. 26, 2007 and published as: US2009/0082841 on Mar. 26, 2009.
Office Action dated Apr. 26, 2011 in U.S. Appl. No. 11/861,756, filed Sep. 26, 2007 and published as: US2009/0082842 on Mar. 26, 2009.

(56) References Cited

OTHER PUBLICATIONS

Office Action Response dated Apr. 5, 2011 in U.S. Appl. No. 11/861,756, filed Sep. 26, 2007 and published as: US2009/0082842 on Mar. 26, 2009.
Office Action dated Jun. 21, 2011 in U.S. Appl. No. 11/861,731, filed Sep. 26, 2007 and published as: US2009/0082847 on Mar. 26, 2009.
Office Action Response dated May 23, 2011 in U.S. Appl. No. 11/861,731, filed Sep. 26, 2007 and published as: US2009/0082847 on Mar. 26, 2009.
Office Action Response dated Oct. 12, 2010 in U.S. Appl. No. 11/861,731, filed Sep. 26, 2007 and published as: US2009/0082847 on Mar. 26, 2009.
Extended European Search Report dated Dec. 16, 2009 in European Application No. 09175398.8 filed: Oct. 15, 2004 and published as: EP 2145607 on Jan. 20, 2010.
International Preliminary Report on Patentability dated Apr. 15, 2010 for International Application No. PCT/US2008/078846 filed on Oct. 3, 2008 and published as WO/2009/046372 on Apr. 9, 2009.
International Search Report and Written Opinion dated Jul. 30, 2009 for International Application No. PCT/US2008/078846 filed on Oct. 3, 2008 and published as WO/2009/046372 on Apr. 9, 2009.
International Preliminary Report on Patentability dated Apr. 8, 2010 for International Application No. PCT/US2008/077714 filed on Sep. 25, 2008 and published as WO/2009/042789 on Apr. 2, 2009.
International Search Report and Written Opinion dated May 1, 2009 for International Application No. PCT/US2008/077714 filed on Sep. 25, 2008 and published as WO/2009/042789 on Apr. 2, 2009.
International Preliminary Report on Patentability dated May 27, 2010 for International Application No. PCT/US2008/083451 filed on Nov. 13, 2008 and published as WO/2009/064923 on May 22, 2009.
International Search Report and Written Opinion dated Jun. 30, 2009 for International Application No. PCT/US2008/083451 filed on Nov. 13, 2008 and published as WO/2009/064923 on May 22, 2009.
International Search Report and Written Opinion dated Mar. 26, 2009 for International Application No. PCT/US2008/077727 filed on Sep. 25, 2008 and published as WO2009/042796 on Apr. 2, 2009.
International Preliminary Report on Patentability dated Apr. 8, 2010 for International Application No. PCT/US2008/077727 filed on Sep. 25, 2008 and published as WO2009/042796 on Apr. 2, 2009.
Office Action dated Jan. 14, 2010 in U.S. Appl. No. 11/861,739, filed Sep. 26, 2007 and published as: US2009/0082841 on Mar. 26, 2009.
Office Action Response dated Jun. 14, 2010 in U.S. Appl. No. 11/861,739, filed Sep. 26, 2007 and published as: US2009/0082841 on Mar. 26, 2009.
Office Action dated Apr. 1, 2010 in U.S. Appl. No. 11/861,756, filed Sep. 26, 2007 and published as: US2009/0082842 on Mar. 26, 2009.
Office Action Response dated Jan. 4, 2010 in U.S. Appl. No. 11/861,731, filed Sep. 26, 2007 and published as: US2009/0082847 on Mar. 26, 2009.
Office Action dated Apr. 14, 2010 in U.S. Appl. No. 11/861,731, filed Sep. 26, 2007 and published as: US2009/0082847 on Mar. 26, 2009.
Extended European Search Report dated Jul. 27, 2010 in European Application No. 10005904.7 filed: Apr. 11, 2002 and published as: EP 2221023 on Aug. 25, 2010.
Office Action dated Aug. 26, 2010 in U.S. Appl. No. 11/861,739, filed Sep. 26, 2007 and published as: US2009/0082841 on Mar. 26, 2009.
Office Action Response dated Sep. 1, 2010 in U.S. Appl. No. 11/861,756, filed Sep. 26, 2007 and published as: US2009/0082842 on Mar. 26, 2009.
Office Action dated Oct. 6, 2010 in U.S. Appl. No. 11/861,756, filed Sep. 26, 2007 and published as: US2009/0082842 on Mar. 26, 2009.
Office Action dated Nov. 23, 2010 in U.S. Appl. No. 11/861,731, filed Sep. 26, 2007 and published as: US2009/0082847 on Mar. 26, 2009.

Non-Final Office Action dated May 19, 2017 in U.S. Appl. No. 14/615,337, filed Feb. 5, 2015 and published as: 2015-0157479 on Jun. 11, 2015.
Request for Continued Examination dated Apr. 3, 2017 in U.S. Appl. No. 14/615,337, filed Feb. 5, 2015 and published as: 2015-0157479 on Jun. 11, 2015.
The AneuRx® Stent Graft System Treatment for AAA brochure, "An Innovative Modular Approach for the Treatment of Abdominal Aortic Aneurysms (AAA)," Medtronic AVE, Inc. 1999.
The AneuRx® Stent Graft Treatment for TAA brochure, "An Endoluminal Solution for the Treatment of Descending Thoracic Aortic Aneurysms," Medtronic, Inc. 1999.
Blum et al. "Abdominal aortic aneurysms: preliminary technical and clinical results with transfemoral placement of endovascular self-expanding stent-grafts" Radiology 198(1):25-31 (1996). ;198(1):25-31 (1996).
Blum et al. "Endoluminal stent-grafts for infrarenal abdominal aortic aneurysms" N Engl J Med 336(1):13-20 (1997). ;336(1):13-20 (1997).
Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.
Canero et al., "Optimal stent implantation: three-dimensional evaluation of the mutual position of stent and vessel via intracoronary echocardiography," Computers in Cardiology, 261-264 (Sep. 1999).
Cooley, Denton A., Surgical Treatment of Aortic Aneurysms (Book), W.B. Saunders Company, West Washington Square, PA (1986).
Donayre, et al., "Fillable endovascular aneurysm repair", Endovascular Today, p. 64-66, Jan. 2009.
Dumoulin C. et al., "Mechanical behavior modeling of balloon expandable stents." Journal of Biomechanics, vol. 33, No. 11, pp. 1461-1470 (available online: Sep. 8, 2000).
Elger et al. "The Influence of Shape on the Stresses in Model Abdominal Aortic Aneurysms," Transactions of the ASME 326:326-32 (1996).
Ernst "Current therapy for infrarenal aortic aneurysms" N. Engl J Med 336(1):58-60 (1997).
Haimovitch, L. and Patierson, N., "Robust growth is forecast for endovascular repair of AAAs," The BBI Newsletter, vol. 26, No. 5, pp. 113-144, (May 2003).
How et al. "Mechanical Properties of Arteries and Arterial Grafts," Chapter 1 of Cardiovascular Biomaterials Hasting, G.W. (ed.) London; New York: Springer-Verlag, 1992 pp. 1-35.
Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).
Mandai, S. et al. (1992). "Direct Thrombosis of Aneurysms with Cellulose Acetate Polymer. Part I: Results of Thrombosis in Experimental Aneurysms," *J. Neurosurgery* 77:497-500.
Mirich et al., "Percutaneously Placed Endovascular Grafts for Aortic Aneurysms: Feasibility Study", Radiology, 170/3:1033-1037 (1989); 1033-1037 (1989).
Moore et al. "Transfemoral endovascular repair of abdominal aortic aneurysm: results of the North American EVT phase 1 trial" J Vasc Surg 23(4):543-553 (1996). ;23(4):543-553 (1996).
Mower et al. "Stress Distributions in Vascular Aneurysms: Factors Affecting Risk of Aneurysm Rupture," J. Surgical Research 55:151-61 (1993).
Office Action dated Oct. 1, 2009 in U.S. Appl. No. 11/861,731, filed Sep. 26, 2007 and published as: US2009/0082847 on Mar. 26, 2009.
Parodi "Endovascular repair of abdominal aortic aneurysms and other arterial lesions" J Vasc Surg 21(4):549-557 (1995).;21(4):549-557 (1995).
Parodi et al., "Transfemoral intraluminal graft implantation for abdominal aortic aneurysms," Ann. Vasc. Surg., 5(6):491-499 (1991).
Perry, M. D. and Chang, R. T., "Finite Element Analysis of Ni-Ti Alloy Stent Deployment," Proceedings of the Second International Conference on SMST, Asilomar Conference Center, Pacific Grove CA. USA (1997).

(56) References Cited

OTHER PUBLICATIONS

Rogers et al., "Balloon-Artery Interactions During Stent Placement: A finite element analysis approach to pressure, compliance and stent design as contributors to vascular injury", 1999 American Heart Association pp. 378-383.
Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).
Uflacker, R. and Robinson, J., "Endovascular treatment of abdominal aortic aneurysms: a review," Eur. Radial.,11:739-753 (2001).
Verhagen "Latest AAA Innovations: The Endurant Stent Graft System", Veith Symposium Nov. 17, 2007.
Verhagen, Hence J.M. "Endurant Medtronic Endograft for EVAR: advantages & early experience", Slides from Veith Symposium Presentation Nov. 22, 2008.
Vos, A.F.W. et al., "Endovascular Grafting of Complex Aortic Aneurysms with a modular site Branch Stent Graft System in a Porcine Model", Eur J Vasc Endovasc Surg, May 2004 vol. 27 492-497.
Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.
Volodos, N.L. et al. (1986) "Self-Fixing Synthetic Prostheisis for Endoprosthesis of Vessels," Vestnik Khigurgii pp. 123-124, Abstract Only in English.
Volodos, N.L. et al. (1989). "Clinical Experience in Use of Self-Fixing Synthetic Prosthesis for Distal and Intraoperative Endoprosthestics of Aora and Iliac Arteries," Theses of Ixth All-Union Symposium (Oct. 2-3, 1989), Abstract only in English, four pages.
Web page, "Drug Eluting Stents—Why Use Drug Eluting Stents?" Polymer Coatings Division; at: URL http://www.lombardmedlcal.co.uk/lombard/pcde.why.html; Lombard Medical; printed Feb. 1, 2005.
Whitcher, "Simulation of in vivo loading conditions of nitinol vascular stent structures", 1997, Elsevier Science Ltd., pp. 1005-1011.
Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).
Wisselink, W. et al. (2001). "Clipping of Inferior Mesenteric and Lumbar Arteries via Retroperitoneal Laparo-Endoscopic Approach as a Treatment of Persistent Endoleak" Chapter 18 in Endoleaks and Endotension, Veith, F.J. et al. eds. Marcel Dekker, Inc. pp. 211-220.
Extended European Search Report dated Jan. 27, 2015 in European Application No. EP 11841183.4 filed: Nov. 15, 2011.
Supplemental European Search Report dated Feb. 13, 2015 in European Application No. EP 11841183.4 filed: Nov. 15, 2011.
Extended European Search Report dated Oct. 8, 2015 in European Application No. EP 13771941.5 filed: Apr. 1, 2013.
Extended European Search Report dated Nov. 9, 2015 in European Application No. EP 13772199.9 filed: Mar. 29, 2013.
International Search Report and Written Opinion dated Feb. 2, 2016 in International Patent Application No. PCT/US2015/057016 filed: Oct. 22, 2015 and published as: WO/2016/065208 on: Apr. 28, 2016.
Notice of Allowance dated Nov. 7, 2014 in U.S. Appl. No. 13/799,207, filed Mar. 13, 2013 and published as: US2013/0268044 on: Oct. 10, 2013.
Office Action Response dated Sep. 25, 2014 in U.S. Appl. No. 13/799,207, filed Mar. 13, 2013 and published as: US2013/0268044 on: Oct. 10, 2013.
Office Action Response dated Aug. 18, 2016 in U.S. Appl. No. 14/615,337, filed Feb. 5, 2015 and published as: 2015-0157479 on Jun. 11, 2015.
Office Action dated Apr. 22, 2016 in U.S. Appl. No. 14/615,337, filed Feb. 5, 2015 and published as: 2015-0157479 on Jun. 11, 2015.
Office Action Response dated Feb. 29, 2016 in U.S. Appl. No. 14/615,337, filed Feb. 5, 2015 and published as: 2015-0157479 on Jun. 11, 2015.
Office Action dated Sep. 28, 2015 in U.S. Appl. No. 14/615,337, filed Feb. 5, 2015 and published as: 2015-0157479 on Jun. 11, 2015.
Office Action dated Oct. 1, 2014 in U.S. Appl. No. 13/297,219, filed Nov. 15, 2011 and published as: US2012/0191174 on: Jul. 26, 2012.
Office Action dated Dec. 31, 2014 in U.S. Appl. No. 11/861,739, filed Sep. 26, 2007 and published as: US2009/0082841 on Mar. 26, 2009.
Office Action Response dated Sep. 11, 2014 in U.S. Appl. No. 11/861,739, filed Sep. 26, 2007 and published as: US2009/0082841 on Mar. 26, 2009.
Office Action dated Mar. 28, 2014 in U.S. Appl. No. 13/297,219, filed Nov. 15, 2011 and published as: US2012/0191174 on: Jul. 26, 2012.
Office Action dated May 22, 2014 in U.S. Appl. No. 11/861,739, filed Sep. 26, 2007 and published as: US2009/0082841 on Mar. 26, 2009.
Office Action dated Jun. 4, 2014 in U.S. Appl. No. 13/799,207, filed Mar. 13, 2013 and published as: US2013/0268044 on: Oct. 10, 2013.
Final Office Action dated Jan. 19, 2011, from U.S. Appl. No. 12/245,620.
Final Office Action dated Mar. 13, 2015, from U.S. Appl. No. 12/245,620.
Non-final Office Action dated Jun. 19, 2014, from U.S. Appl. No. 12/245,620.
Non-final Office Action dated May 14, 2010, from U.S. Appl. No. 12/245,620.
Notice of Allowance dated Aug. 16, 2018, from U.S. Appl. No. 12/245,620.

\* cited by examiner

MODULAR VASCULAR GRAFT FOR LOW PROFILE PERCUTANEOUS DELIVERY

This application is a continuation application of U.S. patent application Ser. No. 12/245,620, filed Oct. 3, 2008, which claims priority under 35 U.S.C. section 119(e) from U.S. provisional application Ser. No. 60/977,617 filed Oct. 4, 2007, by Michael V. Chobotov et al. titled "MODULAR VASCULAR GRAFT FOR LOW PROFILE PERCUTANEOUS DELIVERY" which are incorporated by reference herein in their entirety.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (Mar. 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated. What has been needed are stent graft systems and methods that are adaptable to a wide range of patient anatomies and that can be safely and reliably deployed using a flexible low profile system.

SUMMARY

Some embodiments of a modular endovascular graft assembly include a bifurcated main graft member formed from a supple graft material having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. The network of inflatable channels may be disposed anywhere on the main graft member including the ipsilateral and contralateral legs. The network of inflatable channels may be configured to accept a hardenable fill or inflation material to provide structural rigidity to the main graft member when the network of inflatable channels is in an inflated state. The network of inflatable channels may also include at least one inflatable cuff disposed on a proximal portion of the main graft member which is configured to seal against an inside surface of a patient's vessel. The fill material can also have transient or chronic radiopacity to facilitate the placement of the modular limbs into the main graft member. A proximal anchor member may be disposed at a proximal end of the main graft member and be secured to the main graft member. The proximal anchor member may have a self-expanding proximal stent portion secured to a self-expanding distal stent portion with struts having a cross sectional area that is substantially the same as or greater than a cross sectional area of proximal stent portions or distal stent portions adjacent the strut. At least one ipsilateral graft extension having a fluid flow lumen disposed therein may be deployed with the fluid flow lumen of the graft extension sealed to and in fluid communication with the fluid flow lumen of the ipsilateral leg of the main graft member. At least one contralateral graft extension having a fluid flow lumen disposed therein may be deployed with the fluid flow lumen of the graft extension sealed to and in fluid communication with the fluid flow lumen of the contralateral leg of the main graft member. For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

Some embodiments of a modular endovascular graft assembly include a bifurcated main graft member having an axial length of about 5 cm to about 10 cm formed from a supple graft material. The main graft member has a main fluid flow lumen therein, an ipsilateral leg with an ipsilateral fluid flow lumen in communication with the main fluid flow lumen and with an axial length of at least about 2 cm, a contralateral leg with a contralateral fluid flow lumen in communication with the main fluid flow lumen and with an axial length of at least about 2 cm. The main graft member also includes network of inflatable channels disposed on the main graft member, including the ipsilateral and contralateral legs, which is configured to accept a hardenable fill material to provide structural rigidity to the main graft member when the network of inflatable channels are in an inflated state. The network of inflatable channels may also include at least one inflatable cuff disposed on a proximal portion of the main graft member configured to seal against an inside surface of a patient's vessel. A proximal anchor member may be disposed at a proximal end of the main graft member and secured to the main graft member. The proximal anchor member may have a self-expanding proximal stent portion secured to a self-expanding distal stent portion with struts. At least one ipsilateral graft extension having a fluid flow lumen disposed therein may have the fluid flow lumen of the graft extension sealed to and in fluid communication with the fluid flow lumen of the ipsilateral leg of the main graft member. At least one contralateral graft extension having a fluid flow lumen disposed therein may have the fluid flow lumen of the graft extension sealed to and in fluid communication with the fluid flow lumen of the contralateral leg of the main graft member.

Some embodiments of a method of treating a patient include providing a delivery catheter containing a radially constrained bifurcated main graft member. The main graft member may be formed from a supple graft material which has a main fluid flow lumen therein and which has an ipsilateral leg with an ipsilateral fluid flow lumen in communication with the main fluid flow lumen and a contralateral leg with a contralateral fluid flow lumen in communication with the main fluid flow lumen. The main graft member may also include a network of inflatable channels disposed on the main graft member. Inflatable channels of the network of inflatable channels may be disposed on any portion of the main graft member including the ipsilateral and contralateral legs of the main graft member. The main graft member may also include a proximal anchor member which is disposed at a proximal end of the main graft member and secured to the main graft member. The proximal anchor member may have a self-expanding proximal stent portion secured to a self-expanding distal stent portion. Such a delivery catheter may be axially positioned within the patient's vasculature such that the main graft member within the delivery catheter is disposed coextensively with a vascular defect of the patient's aorta. Once this positioning has been achieved, the proximal anchor member may be deployed so as to radially expand and engage an inner surface of the patient's vasculature and anchor the proximal anchor member to the patient's aorta. Thereafter, the network of inflatable channels of the main graft member may be inflated with an inflation material so as to provide a more mechanically rigid structure of the main graft member. For some embodiments, inflation of the network of inflatable channels may also provide a seal between an outer surface of an inflatable cuff of the main graft member and an inside surface of the patient's body lumen in contact with the inflatable cuff. For some embodiments, a hardenable fill material may be used that may assume or more solid configuration after inflation of the network of inflatable channels so as to provide additional mechanical rigidity as well as prevent leakage of the fill material. Some embodiments may also employ radiopaque inflation material to facilitate monitoring of the fill process and subsequent engagement of graft extensions. A second delivery catheter containing a radially constrained self-expanding contralateral graft extension may then be axially positioned in the contralateral leg of the main graft member with a proximal portion of the contralateral graft extension axially overlapped with an inner fluid flow lumen of the contralateral leg of the main graft member and a distal portion of the contralateral graft extension axially overlapped with a portion of the patient's contralateral iliac artery. Access to the contralateral leg of the main graft portion may be achieved by percutaneous access or femoral arteriotomy from the patient's contralateral femoral artery with a delivery sheath or the like. Once properly positioned, the self-expanding contralateral graft extension may be deployed by releasing the radial constraint of the second delivery catheter. As the contralateral graft extension self expands in an outward radial orientation, a seal between the inner fluid flow lumen of the contralateral graft extension, a fluid flow lumen of the contralateral leg and a fluid flow lumen of the contralateral iliac artery may be formed. A third delivery catheter containing a radially constrained self-expanding ipsilateral graft extension may also be axially positioned in the ipsilateral leg of the main graft member with a proximal portion of the ipsilateral graft extension axially overlapped with an inner fluid flow lumen of the ipsilateral leg of the main graft member and a distal portion of the ipsilateral graft extension axially overlapped with a portion of the patient's ipsilateral iliac artery. The self-expanding ipsilateral graft extension may then be deployed by releasing the radial constraint so as to form a seal between the inner fluid flow lumen of the ipsilateral graft extension, a fluid flow lumen of the ipsilateral leg and a fluid flow lumen of the ipsilateral iliac artery. The ipsilateral and contralateral graft extensions may be delivered and deployed in either order.

Some embodiments of a graft extension include a fluid flow lumen disposed therein, at least one layer of permeable PTFE material, at least one layer of semi-permeable or substantially non-permeable PTFE material having no discernable node and fibril structure and an interposed self-expanding stent formed from an elongate resilient element helically wound with a plurality of longitudinally spaced turns into an open tubular configuration disposed between at least one outer layer and at least one inner layer of PTFE material.

These features of embodiments will become more apparent from the following detailed description when taken in conjunction with the accompanying exemplary drawings.

DETAILED DESCRIPTION

Figure 1:
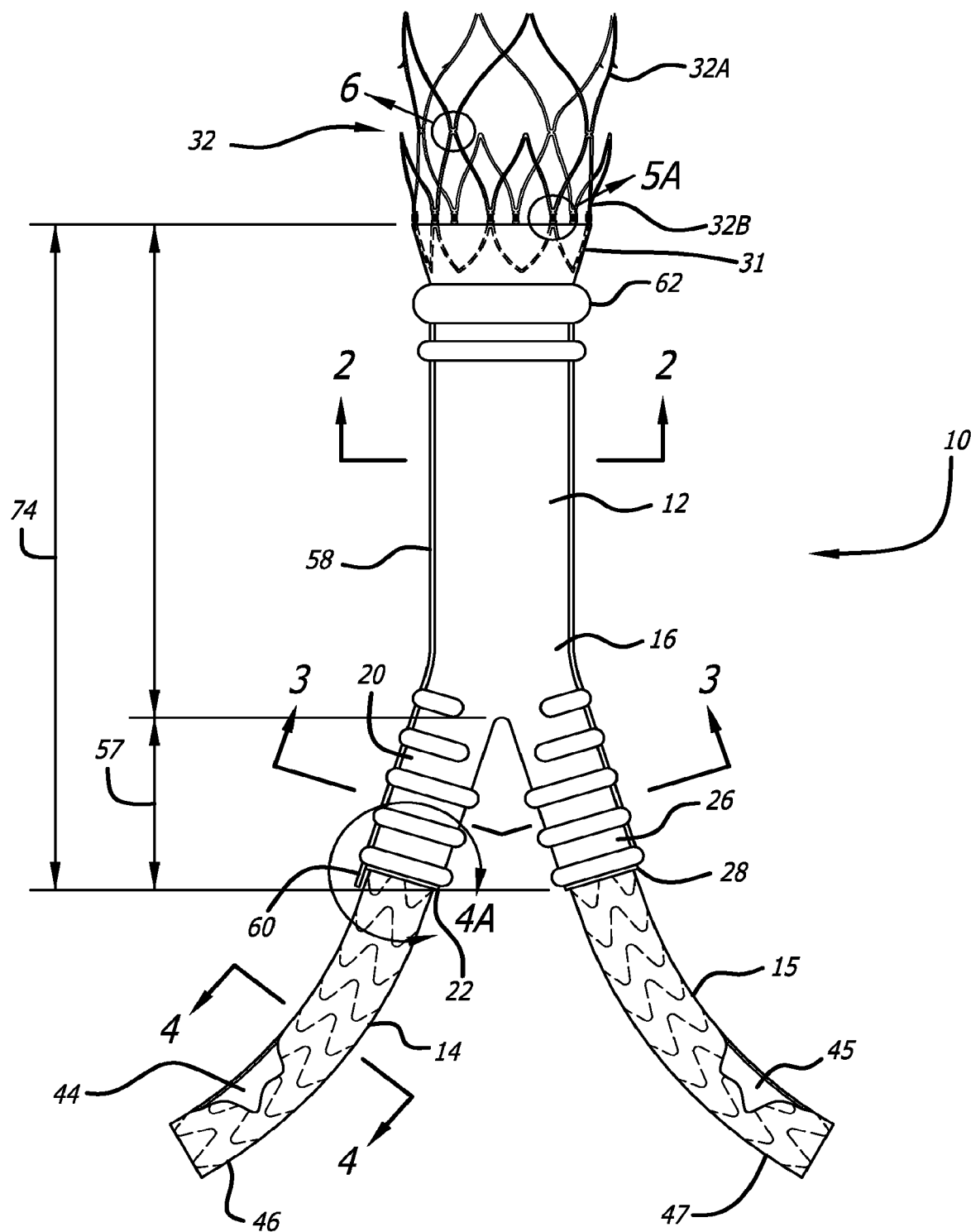
FIG. 1 is an elevation view of a modular graft assembly.

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms.

Some embodiments of a modular endovascular graft assembly may include a bifurcated main graft member formed from a supple graft material, such as ePTFE, having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. For some embodiments, the main graft member may have an axial length of about 5 cm to about 10 cm, more specifically, about 6 cm to about 8 cm in order to span an aneurysm of a patient's aorta without engaging the patient's iliac arteries directly with the legs of the main graft member.

The inflatable channels of the network of inflatable channels may be disposed on any portion of the main graft member including the ipsilateral and contralateral legs. The network of inflatable channels may be configured to accept a hardenable fill material to provide structural rigidity to the main graft member when the network of inflatable channels are in an inflated state and the inflation material has been cured or hardened. Radiopaque inflation material may be used to facilitate monitoring of the fill process and subsequent engagement of graft extensions. The network of inflatable channels may also include at least one inflatable cuff disposed on a proximal portion of the main graft member which is configured to seal against an inside surface of a patient's vessel, such as the aorta.

A proximal anchor member is disposed at a proximal end of the main graft member and secured to the main graft member. The proximal anchor member has a self-expanding proximal stent portion secured to a self-expanding distal stent portion with struts. Some embodiments of the struts may have a cross sectional area that is substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal stent of the proximal anchor member further includes a plurality of barbs having sharp tissue engaging tips that are configured to extend in a radial outward direction in a deployed expanded state. For some embodiments, the proximal anchor member includes a 4 crown proximal stent portion and a 8 crown distal stent portion which may be made from a superelastic alloy such as superelastic NiTi alloy.

At least one ipsilateral graft extension having a fluid flow lumen disposed therein may be deployed with the fluid flow lumen of the graft extension sealed to and in fluid communication with the fluid flow lumen of the ipsilateral leg of the main graft member. In addition, at least one contralateral graft extension having a fluid flow lumen disposed therein may be deployed with the fluid flow lumen of the graft extension sealed to and in fluid communication with the fluid flow lumen of the contralateral leg of the main graft member. For some embodiments, the graft extensions may include an interposed self-expanding stent disposed between at least one outer layer and at least one inner layer of supple layers of graft material. The interposed stent disposed between the outer layer and inner layer of graft material may be formed from an elongate resilient element helically wound with a plurality of longitudinally spaced turns into an open tubular configuration. For some embodiments, the interposed stent is may include a superelastic alloy such as superelastic NiTi alloy. In addition, the graft material of each graft extension may further include at least one axial zone of low permeability for some embodiments.

For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

FIGS. 1-6 show a bifurcated embodiment of a modular graft assembly 10 for treatment of an abdominal aortic aneurysm. The graft assembly 10 includes a bifurcated main graft member 12, an ipsilateral graft extension 14 and contralateral graft extension 15. The main graft 12 has a wall portion 16 that bounds a main fluid flow lumen 18 disposed therein. An ipsilateral leg 20 of the main graft 12 has a ipsilateral port 22 and an ipsilateral fluid flow lumen 24 that is in fluid communication with the main fluid flow lumen 18 and the ipsilateral port 22. A contralateral leg 26 of the main graft 12 has a contralateral port 28 and a contralateral fluid flow lumen 30 that is in fluid communication with the main fluid flow lumen 18 and the contralateral port 28. The main graft 12, ipsilateral leg 20 and contralateral leg 26 form a bifurcated "Y" shaped configuration.

The main fluid flow lumen 18 (shown in FIG. 2) of the main graft 12 generally may have a larger transverse dimension and area than a transverse dimension and area of either of the fluid flow lumens 24 and 30 (shown in FIG. 3) of the ipsilateral leg 20 or contralateral leg 26, respectively. A proximal anchor member 32 is disposed at a proximal end 31 of the main graft 12. The proximal anchor member 32 includes a proximal self-expanding stent 32A that is formed from an elongate element having a generally serpentine shape with four crowns or apices at either end. Each proximal apex or crown of the proximal stent 32A is coupled to alternating distal crowns or apices of an 8 crown distal self-expanding stent 32B. The distal self-expanding stent is formed from an elongate element having a generally serpentine shape. A distal end of the distal stent 32B may be mechanically coupled to a connector ring which is embedded in graft material of the proximal end of the main graft 12, or directly coupled to perforations in the proximal edge region of the main graft. Embodiments of the connector ring may be generally circular in shape have regular undulations about the circumference that may be substantially sinusoidal in shape. The proximal stent 32A includes outwardly extending barbs 33, that may be integrally formed with the struts of the stent for some embodiments, having sharp tissue penetrating tips that are configured to penetrate into tissue of an inside surface of a lumen within which the proximal stent 32A is deployed in an expanded state. Although the proximal anchor member 32 is shown as including self-expanding stents 32A and 32B, similar stents may be used that are configured to be inelastically expanded with outward radial pressure as might be generated by the expansion of an expandable balloon from within either or both stents 32A and 32B. The connector ring coupled to the proximal stent 32B may also be inelastically expandable.

With regard to graft embodiments discussed herein, such as graft assembly 10, and components thereof, as well as graft extensions 14 and 15, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

The ipsilateral graft extension 14 has a fluid flow lumen 44 disposed therein. The ipsilateral graft extension 14 has an outer surface which may be sized and configured to be sealed to an inside surface of the ipsilateral leg of the main graft with the inner fluid flow lumen 44 of the ipsilateral graft extension 14 in fluid communication with the fluid flow lumen 24 of the ipsilateral leg 20. Typically, an outside surface 46 of the graft extension 14 may be sealed to an inside surface 48 of the ipsilateral leg 20 of the main graft 12 when the graft extension 14 is in a deployed state. The contralateral graft extension 15 has a fluid flow lumen 45 disposed therein. The contralateral graft extension 15 has an outer surface 47 which may be sized and configured to be sealed to an inside surface 50 of the contralateral leg 26 of the main graft 12 with the inner fluid flow lumen 45 in fluid communication with the fluid flow lumen 30 of the contralateral leg 26. Typically, an outside surface 47 of the graft extension 15 may be sealed to an inside surface 50 of the contralateral leg 26 of the main graft 12 when the graft extension 15 is in a deployed state. For some embodiments, the axial length of the ipsilateral and contralateral legs 20 and 26 may be sufficient to provide adequate surface area contact between outer surfaces 46 and 47 of graft extensions 14 and 15 and respective inside surfaces 48 and 50 of the legs 20 and 26 to provide sufficient friction to hold the graft extensions 14 and 15 in place. Varying the amount of overlap between the legs and extensions can allow for different effective overall graft lengths to be achieved, thereby accommodating a range of anatomical sizes with fewer distinct main body and extension dimensions than would otherwise be required. For some embodiments, the ipsilateral and contralateral legs 20 and 26 may have an axial length of at least about 1 cm. For some embodiments, the ipsilateral and contralateral legs 20 and 26 may have an axial length of about 2 cm to about 6 cm, more specifically, about 3 cm to about 5 cm.

The graft extensions 14 and 15 may be formed from an inner layer or layers and outer layer or layers of flexible graft material, such as PTFE or ePTFE. The inner and outer layers of graft material may be formed from tubular extrusions, laminated wraps of multiple layers of graft material or materials, and the like. The inner or outer layers of graft material may be permeable, semi-permeable or substantially non-permeable for some embodiments. For some embodiments, the nominal length of the extensions 14 and 15 may be permeable with one or more longitudinal sections, such as a middle longitudinal section, being semi-permeable or non-permeable. Some embodiments of the graft extensions 14 and 15 may have an overall tapered or flared configuration with a nominal inner lumen that tapers or flares when the graft extension is in a relaxed expanded state. For embodiments that include laminated wraps of material, the wraps may be carried out circumferentially, helically or in any other suitable configuration.

A radially expandable stent 51 may be interposed between the outer layer 54 and inner layer 56 of graft material of extensions 14 and 15. The interposed stent disposed between the outer layer and inner layer of graft material may be formed from an elongate resilient element helically wound with a plurality of longitudinally spaced turns into an open tubular configuration. The helically wound stent 51 may be configured to be a self-expanding stent or radially expandable in an inelastic manner actuated by an outward radial force from a device such as an expandable balloon or the like. Some tubular prosthesis embodiments that may be used for graft extensions 14 and 15 are discussed in U.S. Pat. No. 6,673,103 to Golds et al., filed May 16, 2000 titled "Mesh and Stent for Increased Flexibility", which is hereby incorporated by reference in its entirety herein.

The graft extensions 14 and 15 may optionally include attachment elements disposed on outer surfaces 46 and 47 (shown in FIG. 3) of their respective proximal ends or sections that may be used to couple to corresponding attachment elements disposed on inside surfaces of the respective ipsilateral leg 20 and contralateral leg of the main graft 12. Attachment element embodiments that may be used on outside surfaces 46 and 47 of the graft extensions 14 and 15 and inside surfaces 48 and 50 of legs 20 and 26 of the main graft 12 may include any of the attachment elements in International Patent Application No. PCT/US2005/008119, entitled "Modular Endovascular Graft", filed Mar. 11, 2005, by Stephens, et al., published Sep. 22, 2005, which is hereby incorporated by reference herein in its entirety. Some embodiments of modular grafts such as system 10 having attachment elements may include a first graft body section such as graft main body 12 and a second graft body section such as extensions 14 and 15. The first graft body section may have a first wall portion and a first attachment element disposed on the first wall portion and the second graft body section may have a second attachment element disposed on a second wall portion of the second graft body section. The second attachment element may be configured to be secured to the first attachment element with respective fluid flow lumens of the first and second graft body sections sealed together. For some embodiments, the first and second attachment elements may be secured together in an overlapped portion of the first and second graft body sections. For some embodiments, the first attachment element may include a plurality of flexible hooks and the second attachment element includes a plurality of flexible loops adjacent each other wherein the flexible hooks are configured to mechanically engage the flexible loops when the first and second attachment elements are pressed together. For some embodiments, the first attachment element includes a plurality of buttons having an enlarged head portion regularly spaced from each other on a surface a first wall portion and a second attachment element includes an expandable mesh having a plurality of apertures configured to allow entry of the enlarged head portion of the buttons while the mesh is in a circumferentially constrained state and to capture the enlarged head portion of the buttons when the mesh is in a circumferentially expanded state. For some embodiments, the first attachment element includes a plurality of pins radially extending from a surface of a first wall portion and the second attachment element includes an expandable mesh having a plurality of apertures configured to allow entry of the pins when the first attachment element is pressed against the second attachment element. For some embodiments the first attachment element may include an inflatable cuff containing curable material and the second attachment element includes an expandable member with barbs configured to extend outwardly into the inflatable cuff and curable material.

The transverse dimension or diameter of the main fluid flow lumen 18 of some main graft embodiments 12 in a radially expanded state may be from about 12.0 mm to about 32.0 mm. The transverse dimension or diameter of the ipsilateral and contralateral fluid flow lumens 24 and 30 of the respective ipsilateral leg 20 and contralateral leg 26 may be from about 5 mm to about 20 mm for some embodiments. The axial length of the contralateral leg 26 is indicated by arrow 57 in FIG. 1. For some embodiments, the length of the legs 20 and 26 and may be from about 2 cm to about 6 cm. The transverse dimension of some embodiments of the graft extensions 14 and 15 when in a radially expanded state may be from about 5 mm to about 26 mm. The axial length of some embodiments of the graft extensions 14 and 15 may be from about 2 cm to about 15 cm, specifically, about 5 cm to about 10 cm. Some embodiments of the ipsilateral and contralateral extension grafts 14 and 15 may have outer transverse dimensions or diameters of between about 10 mm to about 30 mm, more specifically, between about 15 mm and 25 mm when in an expanded state.

The main graft 12 and ipsilateral graft extensions 14 and 15 may be made at least partially from polytetrafluoroethylene (PTFE) which may include expanded polytetrafluoroethylene (ePTFE). In particular, main graft 12 and graft extensions 14 and 15 may include any number of layers of PTFE and/or ePTFE, including from about 2 to about 15 layers, having an uncompressed layered thickness of about 0.003 inch to about 0.015 inch for the supple graft material or materials alone without supporting or ancillary structures such as high strength stents, connector rings or the like. Unless otherwise specifically stated, the term "PTFE" as used herein includes PTFE, porous PTFE and ePTFE, any of which may be impermeable, semi-permeable, or permeable. Furthermore, the graft assembly and any portions thereof including the main body and extensions described herein may include all PTFE, all ePTFE, or a combination thereof. Such graft body sections may also include any alternative high strength, supple biocompatible materials, such as DACRON, suitable for graft applications. Descriptions of various constructions of graft body sections as well as other components of graft assembly 10 that may be used in any suitable combination for any of the embodiments discussed herein may be found in U.S. patent application Ser. No. 10/029,557, publication US 2003/0116260 A1, filed Dec. 20, 2001 by Chobotov, et al., entitled "Method and Apparatus for Manufacturing an Endovascular Graft Section", U.S. patent application Ser. No. 10/029,584, filed Dec. 20, 2001 by Chobotov et al., entitled "Endovascular Graft Joint and Method of Manufacture", U.S. patent application Ser. No. 10/029,559, entitled "Method and Apparatus for Shape Forming Endovascular Graft Material", filed on Dec. 20, 2001 by Chobotov et al., U.S. Pat. No. 7,147,660, filed Dec. 20, 2002, by Chobotov et al., entitled "Advanced Endovascular Graft", U.S. patent application Ser. No. 11/106,131, publication US 2006/0233990A1, filed Apr. 13, 2005, by Humphrey et al. entitled "PTFE Layers and Methods of Manufacturing", and U.S. patent application Ser. No. 11/106,150, publication US 2006/0233991, filed Apr. 13, 2005, by Humphrey et al., entitled "PTFE Layers and Methods of Manufacturing", the entirety of each of which is incorporated herein by reference.

The laminated structure of various portions of the graft member 12, including ipsilateral and contralateral legs 20 and 26, extensions 14 and 15, or all of these, may include a variety of configurations wherein laminate materials having similar but different properties may be used together or individually. For example, some embodiments of a main body portion of the graft member 12 may have a laminated structure of about 1 layer to about 5 layers of porous ePTFE material having a mean nodal spacing of about 5 microns to about 35 microns, more specifically, about 10 microns to about 25 microns, and a thickness of about 0.0002 inches to about 0.002 inches, more specifically, about 0.0005 inches to about 0.0015 inches. The main body portion of the graft member 12 may also include about 1 layer to about 5 layers of semi-permeable PTFE having a first permeability and a thickness of about 0.0002 inches to about 0.002 inches, more specifically, about 0.0004 inches to about 0.001 inches. The main body portion may also include about 1 layer to about 5 layers of semi-permeable PTFE material having a second permeability different from the first permeability and a thickness of about 0.0002 inches to about 0.002 inches, more specifically, about 0.0004 inches to about 0.001 inches. Any suitable embodiments of the semi-permeable layers of PTFE discussed in U.S. Patent Applications 2006/0233990 and 2006/0233991, incorporated by reference above, may be used in these embodiments. The main body portion may also include about 1 layer to about 5 layers of PTFE having essentially no nodal spacing and very low or no liquid permeability and a thickness of about 0.0001 inches to about 0.0015 inches, more specifically, about 0.0002 inches to about 0.001 inches.

For embodiments of modular graft systems that do not include the attachment elements, outside surfaces 46 and 47 of the proximal ends of the graft extensions 14 and 15 may be expanded against the inside surfaces 48 and 50, respectively, of the fluid flow lumens of legs 20 and 26 of the graft member 12. This configuration may be used to seal the fluid flow lumens 44 and 45 of the graft extensions 14 and 15 to the fluid flow lumens 24 and 30 of the legs 20 and 26. Expandable members, such as expandable anchor members and the like, may be used to expand the graft extensions 14 and 15 against the inside surfaces 48 and 50 of the fluid flow lumens 24 and 30 of the legs 20 and 26.

A network of inflatable elements or channels 58 is disposed on the main graft 12 which may be inflated under pressure with an inflation material (not shown) through a main fill port 60 that has a lumen disposed therein in fluid communication with the network of inflatable channels 58. The inflation material may be retained within the network of inflatable channels 58 by a one way-valve (not shown), disposed within the lumen of the main fill port 60. The network of inflatable channels 58 may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the main graft 12 and legs by virtue of the mechanical properties of the hardened material disposed within the channels. The network of inflatable channels 58 may also provide structural support to the main graft 12 when in an inflated state due to the stiffness of the channels created by the increased interior pressure within the channels even if a non-hardenable inflation material, such as saline or the like, is used so long as an increased interior pressure can be maintained. Such an increase in stiffness or rigidity may be useful for a variety of purposes. For example, during deployment, inflation of the network of inflatable channels may urge the main graft body including the main flow channel and legs thereof to conform to a generally cylindrical configuration having open flow lumens which may be useful when attempting to locate and navigate the flow lumens of the contralateral or ipsilateral leg with a delivery catheter, guidewire or the like. Such location and navigation of the flow lumens of the main graft body and portions thereof may also be facilitated by the use of radiopaque inflation materials that provide enhanced visualization under fluoroscopic imaging.

The network of inflatable channels 58 may include one or more circumferential channels disposed completely or partially about the main graft or legs of the main graft as well as longitudinal or helical channels that may provide support as well as a conduit in communication with the circumferential channels that may be used for filling the network of inflatable channels with inflation material. Some embodiments may also employ radiopaque inflation material to facilitate monitoring of the fill process and subsequent engagement of graft extensions. The network of inflatable channels 58 may also include one or more one or more enlarged circumferential channels in the form of inflatable cuffs, such as proximal inflatable cuff 62, which may be configured to seal to an inside surface of a patient's vessel such as a patient's abdominal aorta. Proximal inflatable cuff 62 is disposed on a proximal portion of the main graft 12 distal of the proximal anchor member 32 and has an outer surface that extends radially from a nominal outer surface of the main graft 12. The inflatable cuff 62 may be configured to expand radially beyond a nominal outer surface of the main graft 12 and provide a seal against an inside surface of a body lumen when the inflatable cuff 62 is inflated with an inflation material to an expanded state. The axial separation of the proximal anchor member 32 and proximal inflatable cuff 62 allows for spatial separation of the primary anchoring mechanism and at least part of the sealing function which may allow the graft to be restrained or otherwise compressed to a smaller outer profile for deployment from a delivery catheter. An interior cavity of the inflatable cuff 62 is in fluid communication with the interior cavity of the remaining network of inflatable channels and may have a transverse dimension or inner diameter of about 0.040 inch to about 0.250 inch.

Some embodiments of main graft member 12 may include about 1 to about 8 circumferential inflatable channels disposed about each leg 20 and 26 and about 1 to about 8 circumferential channels disposed about a main body portion of the main graft member 12. Some embodiments of the main graft body member 12 may include about 1 to about 4 longitudinal or axial inflatable channels that may serve to connect the circumferential inflatable channels. Some embodiments of the circumferential channels may extend a full circumference of the graft section upon which they are disposed, or they may extend only partially around the graft section upon which they are disposed. For the main graft member embodiment 12 shown in FIG. 1, the network of inflatable channels 58 includes the inflatable cuff 62 disposed adjacent the proximal end of the main body portion of the main graft member 12 and a circumferential channel disposed just distal of the inflatable cuff 62. Each leg 20 and 26 of the main graft member 12 includes 3 complete circumferential inflatable channels in axial series. Each leg 20 and 26 also has two partial circumferential inflatable channels disposed proximal of the complete circumferential inflatable channels. A longitudinal or axial channel extends substantially along the ipsilateral side of the main graft member 12 in fluid communication with the fill port 60 and circumferential channels of the ipsilateral leg 20 and the circumferential channels and inflatable cuff 62 at the proximal end of the main body portion. Another axial channel extends along the entire contralateral side of the main graft member 12 in fluid communication with the cuff 62, circumferential channel at the proximal end of the main body portion and the circumferential channels of the contralateral leg 26.

Some of the inflatable channels of the graft member embodiments discussed herein may be disposed circumferentially and axially such as shown in the embodiment of FIG. 1. Alternatively, such inflatable channels may be disposed in spiral, helical, or other configurations. Examples of channel configurations suitable for embodiments of the present invention are described further in commonly-owned pending U.S. patent application Ser. No. 10/384,103, filed Mar. 6, 2003 and entitled "Kink Resistant Endovascular Graft" to Kari et al., the entirety of which is incorporated herein by reference. All inflatable channel embodiments described herein as circumferential, may alternatively take on any of the aforementioned alternative configurations. Other modular graft embodiments are discussed in pending U.S. patent application Ser. Nos. 11/097,718, 2006/0224232, by Chobotov et al. titled "Hybrid Modular Endovascular Graft", filed Apr. 1, 2005, which is hereby incorporated by reference herein in its entirety.

The inflatable cuff 62 and other network of inflatable channels 58 may be filled during deployment of the graft with any suitable inflation material. As discussed above, the inflation material may be used to provide outward pressure or a rigid structure from within the inflatable cuff 62 or network of inflatable channels 58. Biocompatible gases, liquids, gels or the like may be used, including curable polymeric materials or gels, such as the polymeric biomaterials described in pending U.S. patent application Ser. No. 09/496,231 filed Feb. 1, 2000, and entitled "Biomaterials Formed by Nucleophilic Addition Reaction to Conjugated Unsaturated Groups" to Hubbell et al. and pending U.S. patent application Ser. No. 09/586,937, filed Jun. 2, 2000, and entitled "Conjugate Addition Reactions for Controlled Delivery of Pharmaceutically Active Compounds" to Hubbell et al. and further discussed in commonly owned pending U.S. patent application Ser. No. 10/327,711, filed Dec. 20, 2002, and entitled "Advanced Endovascular Graft" to Chobotov, et al., each of which is incorporated by reference herein in its entirety. Some embodiments may use inflation materials formed from glycidyl ether and amine materials, as discussed in U.S. patent application Ser. No. 11/097,467, publication number 2006/0222596, filed Apr. 1, 2005, and entitled "Non-Degradable, Low-Swelling, Water Soluble Radiopaque Hydrogel Polymer" to Askari and Whirley. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

Other inflation materials that may be used for some embodiments include polyethylene oxide materials and neopentyl glycol diacrylate materials which are discussed in U.S. Pat. Nos. 6,610,035 and 6,176,849, which are incorporated by reference herein in their entirety. U.S. Pat. No. 7,147,660 discussed above also includes inflation material embodiments that may be used for embodiments discussed herein.

Figure 1A:
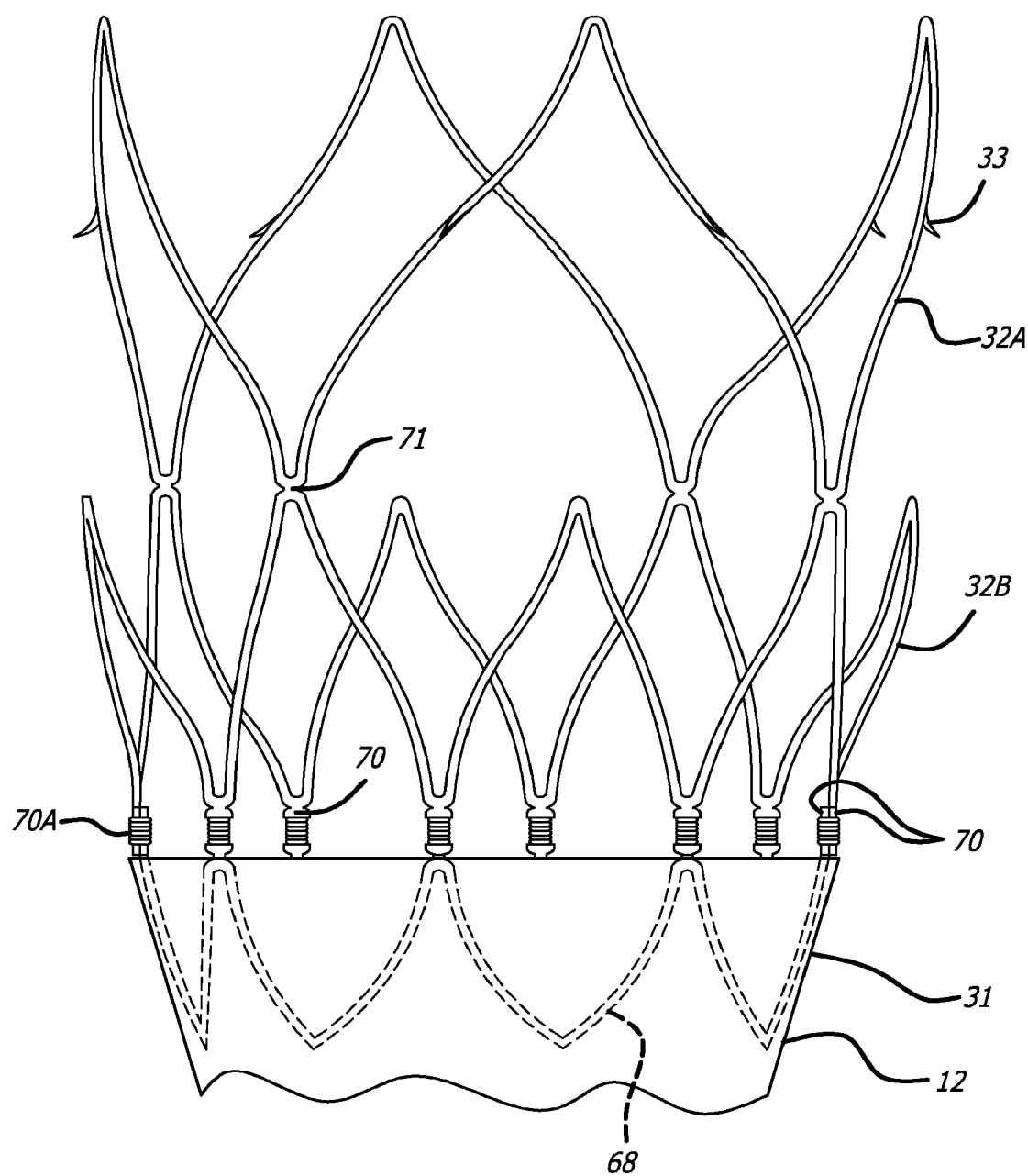
FIG. 1A is an elevation view of a proximal anchor member and connector ring of the modular graft assembly.
Figure 2:
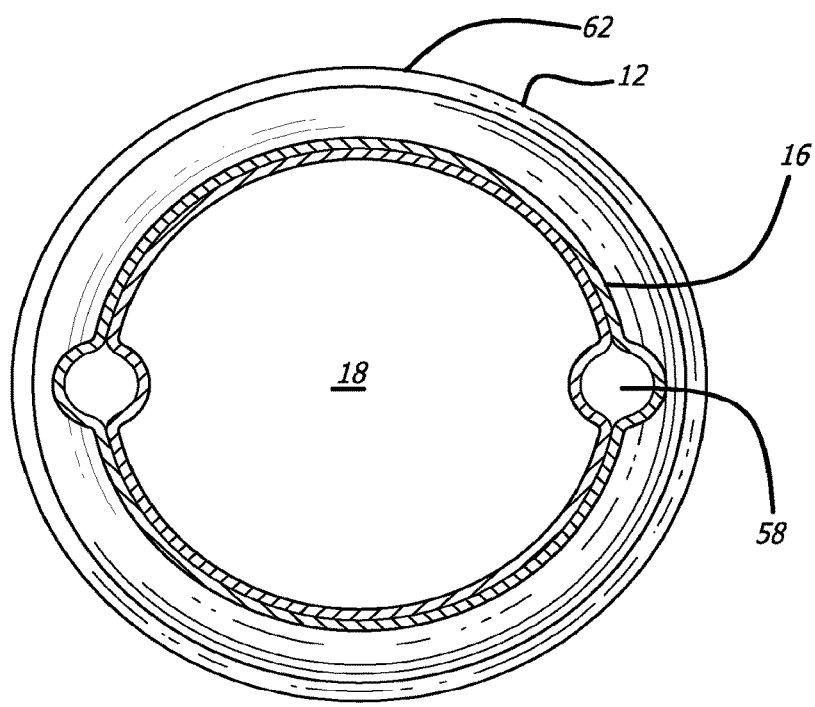
FIG. 2 is a transverse cross section of the modular graft assembly of FIG. 1 taken along lines 2-2 of FIG. 1.
Figure 3:
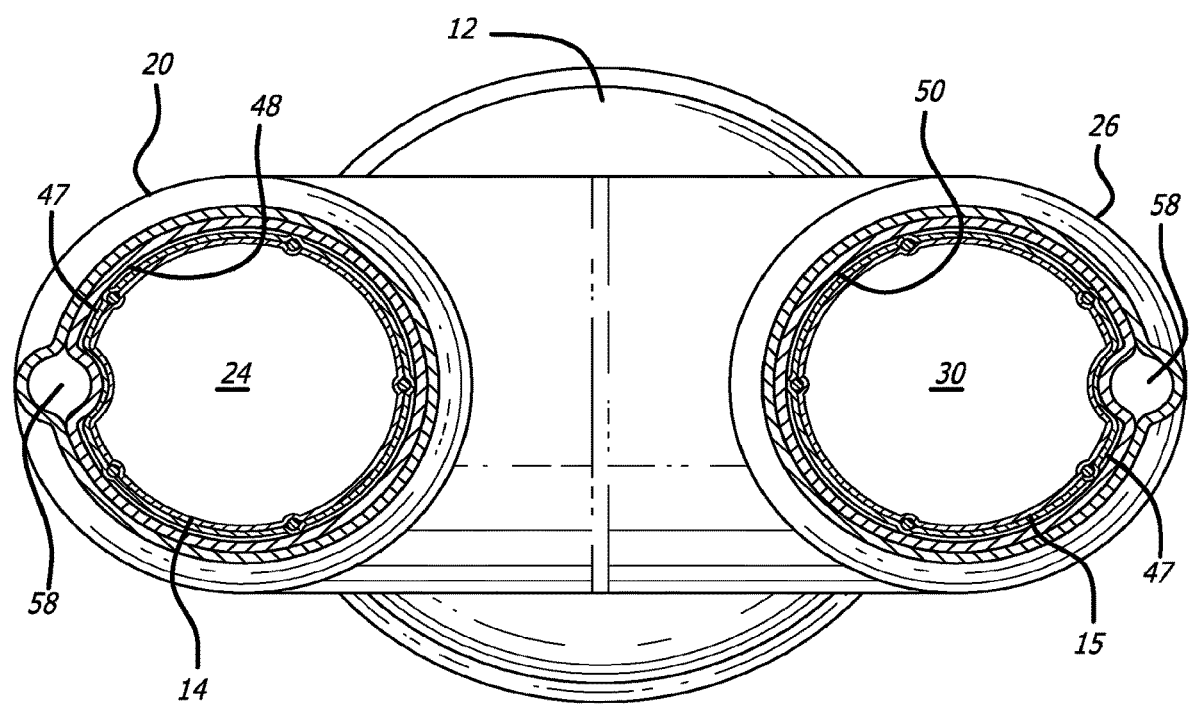
FIG. 3 is a transverse cross section of the modular graft assembly of FIG. 1 taken along lines 3-3 of FIG. 1.

Referring to FIG. 1A, the proximal anchor member 32 may be disposed on a proximal end of the main graft 12 and be secured to the connector ring 68 which is at least partially disposed on a proximal portion of the main graft 12. For some embodiments, the connector ring 68 may be embedded in the graft material of the proximal section of the main graft 12 and may also be secured by one or more flap elements of a PTFE layer or layers adjacent the connector ring 68. The flaps of adjacent layers may be folded over the connector ring and secured to the connector ring 68, adjacent layers of PTFE material or both. Adhesive materials such as FEP or the like may also be used to secure the connector ring 68 to the main graft body 12. The proximal connector ring 68 has connector elements 70 extending proximally from the connector ring 68 beyond the proximal end of the graft material of the main graft 12. The connector elements may be used to couple or be otherwise be secured to mating connector elements of the proximal anchor member 32 which extend distally from the distal side of the distal stent 32B of the proximal anchor member 32. The proximal anchor member 32 may have a cylindrical or ring-like configuration generally with elongate elements of the proximal and distal stents 32A and 32B of the anchor member being preformed in a serpentine or sine wave pattern of the cylinder. The proximal anchor member may have a transverse dimension or diameter that allows for anchoring in a variety of body lumen configurations. Some embodiments of a proximal anchor member 32 which may be suitable for use in a patient's abdominal aorta may have a transverse dimension or diameter of about 20 mm to about 40 mm. The elongate elements that form the proximal anchor member 32 may have a radial thickness of about 0.005 inch to about 0.040 inch. The width of the elongate elements that form the proximal anchor member 32 may be from about 0.01 inch to about 0.2 inch. U.S. Pat. No. 7,147,660 discussed above also includes anchor member embodiments that may be used for embodiments discussed herein.

Figure 5A:
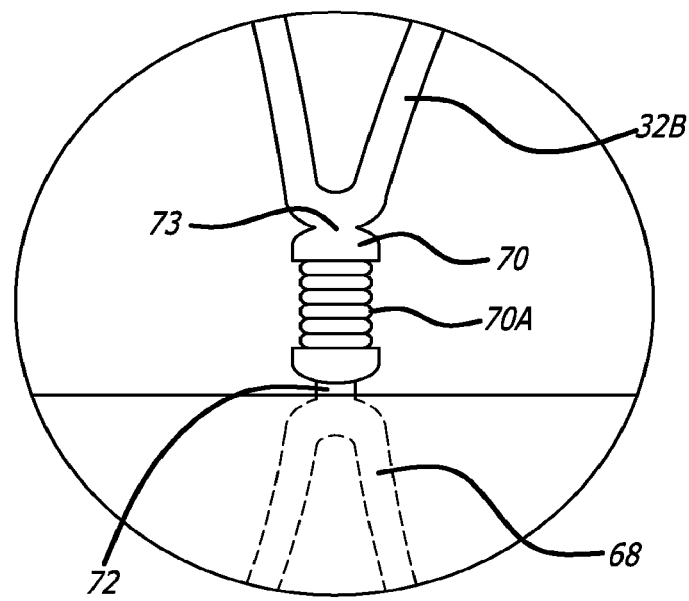
FIG. 5A is an enlarged view of a junction between a proximal anchor member and connector ring of FIG. 1 indicated by the encircled portion 5A-5A in FIG. 1.
Figure 5B:
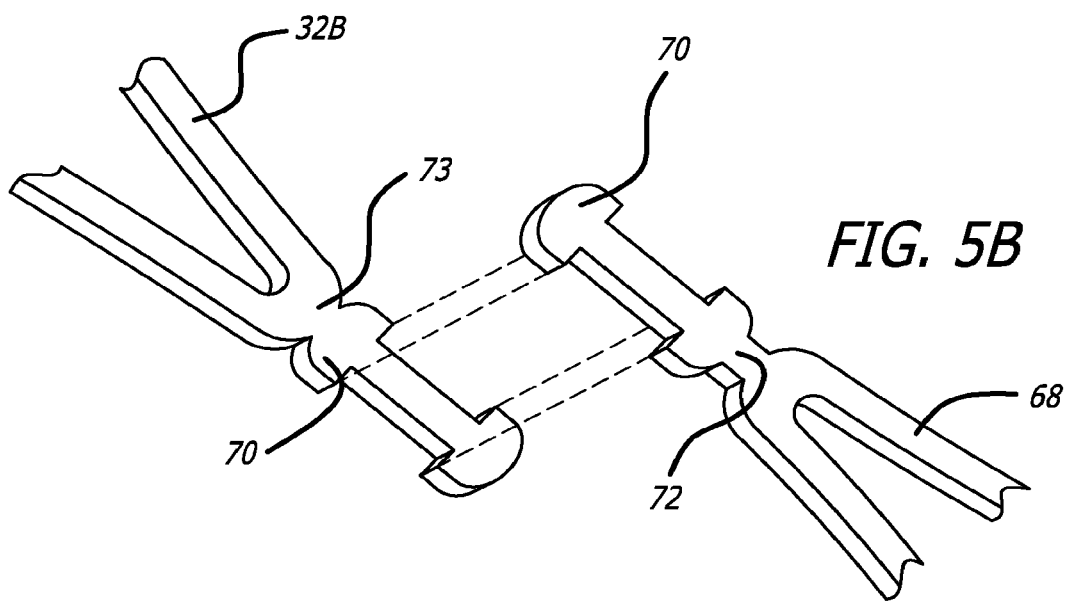
FIG. 5B is an exploded view of a junction between connector elements of the proximal anchor member and connector ring without a coil member.
Figure 6A:
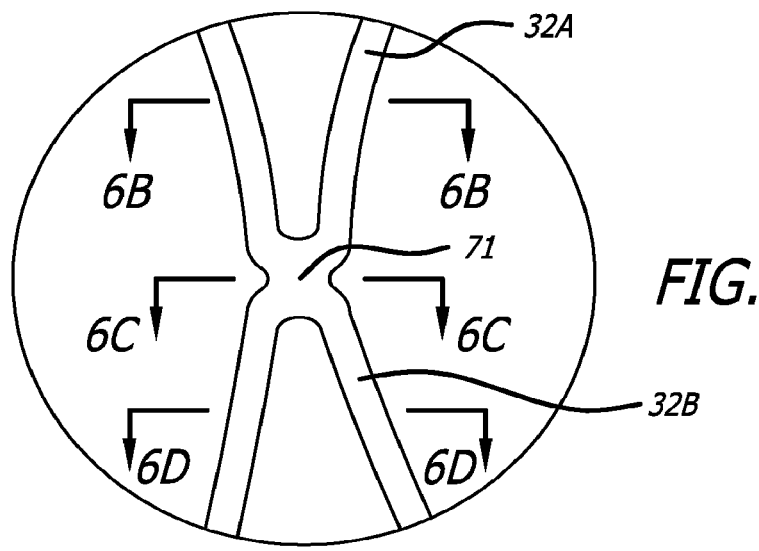
FIG. 6A is an enlarged view of a junction between a distal stent portion and a proximal stent portion of the proximal anchor member of FIG. 1 indicated by the encircled portion 6A-6A in FIG. 1.
Figure 6B:
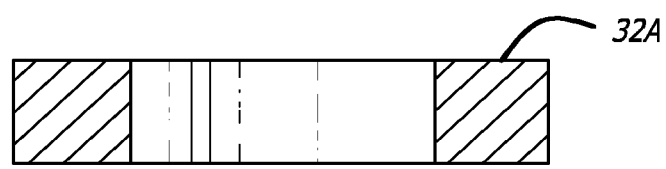
FIG. 6B is a transverse cross section of the proximal anchor member of the modular graft assembly of FIG. 1 taken along lines 6B-6B of FIG. 6A.
Figure 6C:
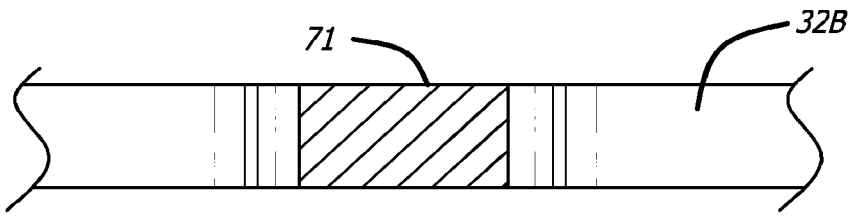
FIG. 6C is a transverse cross section of the proximal anchor member of the modular graft assembly of FIG. 1 taken along lines 6C-6C of FIG. 6A.
Figure 6D:
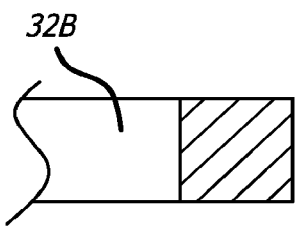
FIG. 6D is a transverse cross section of the proximal anchor member of the modular graft assembly of FIG. 1 taken along lines 6D-6D of FIG. 6A.
Figure 6D:
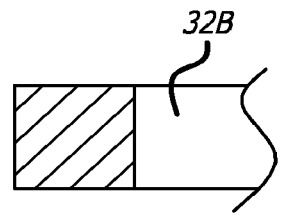

The proximal anchor member 32 is secured to the connector ring 68 with flanged connector elements 70 as shown in FIGS. 5A and 5B. The flanged connector elements 70 may be secured together with wire coils 70A configured to fit between ears of the flanged portions of the connector elements 70 that have a transverse dimension that is greater than a middle portion of the connector elements 70. The flanged portions provide a pair of opposed surfaces for the coil 70A to seat against and mechanically capture two adjacent connector elements 70 together. The wire coils 70A used to coupled the flanged elements may have an inner transverse dimension of about 0.005 inch to about 0.050 inch, more specifically, about 0.010 inch to about 0.030 inch, and have an axial length of about 2 to about 15 times their diameter, more specifically, about 4 to about 8 times their diameter.

Referring again to FIG. 1A, the proximal stent 32A is coupled to the distal stent 32B of the proximal anchor member 32 with struts 71 disposed between adjacent crowns of the two stents which are shown in more detail in FIGS. 6A-6D. The struts may be configured such that the cross sectional area of the material of the stents 32A and 32B and struts remains substantially constant from the proximal portion of the distal stent to the distal portion of the proximal stent. For some embodiments, the cross sectional area of the material in the area of the struts 71 is greater than the cross sectional area of either the proximal stent 32B or distal stent 32A adjacent the struts 71. Such a configuration may be useful in avoiding stress and strain concentrations at the junctions between the proximal and distal stents 32A and 32B.

A similar structural configuration may be used at the junction between the connector ring 68 and the distal end of the distal stent 32B. For this junction, the struts 72 disposed between the connector ring 68 and connector elements 70, as shown in FIG. 5A, may have a cross sectional area substantially the same as or greater than the cross sectional area of the connector ring 68 adjacent the connector element 70. In addition, the struts 73 disposed between the distal end of the distal stent 32B and the connector elements 70 of the distal stent 32B may have a cross sectional area that is substantially the same or greater than the cross sectional area of the distal stent 32B adjacent the strut 73. This configuration may be useful in avoiding stress and strain concentrations in the junction between the connector ring 68 and the distal stent 32B of the proximal anchor member 32.

The proximal anchor member 32 and components thereof may have a variety of configurations which may be collapsible to a small transverse dimension or diameter for percutaneous or other types of delivery and be expandable to engage the inside surface of the patient's vasculature to provide anchoring to the vasculature and prevent or oppose axial movement of the anchor member or the graft section attached thereto. Anchor member embodiments 32 may be configured as a self-expanding anchor member having an undulating pattern and may be made from stainless steel, nickel titanium alloy or any other suitable material. The anchor member 32 may be configured to be balloon expandable or self-expanding in an outward radial direction from a radially compressed state. The distal anchor member 32 and connector ring 68 may be formed by cutting the configuration of these elements from a single tubular piece of a selected material, such as the materials discussed above. The proximal stent 32A of the anchor member 32 may also optionally include barbs 33 that are angled outwardly from the anchor members and are configured to engage tissue of the vessel wall and prevent axial movement of the anchor members once deployed. The proximal anchor member 32 and proximal and distal stents 32A and 32B thereof may have the same or similar features, dimensions or materials to those of the stents described in U.S. patent application Ser. No. 10/327,711, US 2003/0125797 A1, filed Dec. 20, 2002, by Chobotov et al. which is hereby incorporated by reference in its entirety. The distal stent 32B of anchor member 32 may also be secured to connector ring 68 in the same or similar fashion as described in the incorporated application above.

It may be useful for some embodiments of the main graft 12 to have a nominal axial length which is configured to allow the use of the main graft 12 in a wide variety of vascular morphologies with supplementation by one or more graft extensions 14 and 15. A modular graft embodiment 10 is normally chosen in order to have a proper fit to the patient's vasculature. For some graft indications, it is necessary to produce a large number of size variations of the graft system, or graft assembly 10 components, in order to accommodate the size and configuration variations of each patient's vasculature in order to achieve an acceptable fit of the graft assembly 10 within the patient's vasculature. This can be very costly and time consuming for the manufacturer of the endovascular graft assembly 10 and the hospitals which must maintain a comprehensive inventory of the devices. In addition, this may require an inconvenient amount of shelf space in the hospital operating room or catheter lab. For some embodiments, main graft member 12 may have an axial length that is selected to allow anchoring of the proximal anchor member 32 adjacent the renal arteries extending from a patient's aorta with the legs of the bifurcated portion remaining clear of the iliac arteries in a large cross section of patients having diverse physical size and vascular configurations. In this way, the need for customizing a graft assembly 10 for a particular patient or group of patients can be avoided.

For some embodiments, the axial length of the main graft member 12, and particularly the axial distance or separation between the proximal anchor member 32 and distal end of the ipsilateral and contralateral legs 20 and 26 may be selected to extend across an abdominal aortic aneurysm without extending into the iliac arteries of a selected patient. A selected patient may be a member of a group of patients who has the longest axial separation between the sealing point in the aorta just distal to the renal arteries and a distal most viable anchor and sealing point in the iliac arteries. In some embodiments for a particular patient group, the proximal end of the main graft member 12 is axially separated from the distal ends of the ipsilateral and contralateral legs 20 and 26 by a length of about 5 cm to about 10 cm, more specifically, about 6 cm to about 8 cm, as indicated by the arrow 74 in FIG. 1.

For some embodiments of sizing a main graft member embodiment 12, the separation of the proximal anchor member 32 and distal end of deployed graft extensions 14 and 15 is selected such that the separation is just long enough to span the separation between the renal arteries and the proximal most anchor and sealing point in the iliac artery or arteries of a patient. This distance may be determined from the patient, in a selected group of patients, that has the longest such separation in the selected group of patients. In addition, for these embodiments, this separation must be shorter than the separation between the renal arteries and hypogastric artery or arteries. The distance may be determined from the patient, in the selected group of patients, that has the shortest such separation in the selected group of patients. In this way, it may be possible to treat all members of a selected group of patients with a main graft member 12 embodiment or embodiments which have a common main graft body length. Such embodiments may be anchored to the patient's aorta distal of the patient's renal arteries and anchored distally in the patient's iliac artery or arteries, without blocking either the renal arteries or hypogastric artery or arteries. Such a modular graft system embodiment 10 may have an overall length including the main graft member 12 and deployed graft extensions 14 and 15 of about 10 cm to about 22 cm, specifically, about 11 cm to about 20 cm.

The careful sizing and configuring of the main graft 12 allows the use of a single main graft 12 embodiment or design to be adaptable to a wide range of patients when supplemented by one or more graft extensions 14 and 15. More specifically, a main graft 12 having an axial length of about 5 cm to about 8 cm may be properly deployed in a large percentage of potential patients. Once deployed, the fluid flow lumens 24 and 30 of the ipsilateral and contralateral legs 20 and 26 of the main graft 12 can then be sealed to the patient's iliac arteries with the deployment of graft extensions 14 and 15. Although the graft assembly 10 includes the option of using attachment elements to secure the graft extensions 14 and 15 to the ipsilateral leg and contralateral leg of the main graft 12, this may not be necessary in most cases and an adequate seal and mechanical fixation of a graft extensions 14 and 15 may be achieved with the use of a standard expandable member on the graft extensions 14 and 15 instead of an attachment element.

Some embodiments of a method of treating a patient include providing a delivery catheter containing a radially constrained bifurcated main graft member. The main graft member may be formed from a supple graft material which has a main fluid flow lumen therein and which has an ipsilateral leg with an ipsilateral fluid flow lumen in communication with the main fluid flow lumen and a contralateral leg with a contralateral fluid flow lumen in communication with the main fluid flow lumen. The main graft member may also include a network of inflatable channels disposed on the main graft member. Inflatable channels of the network of inflatable channels may be disposed on any portion of the main graft member including the ipsilateral and contralateral legs of the main graft member. The main graft member may also include a proximal anchor member which is disposed at a proximal end of the main graft member and secured to the main graft member. The proximal anchor member may have a self-expanding proximal stent portion secured to a self-expanding distal stent portion.

Such a delivery catheter may be axially positioned within the patient's vasculature such that the main graft member within the delivery catheter is disposed coextensively with a vascular defect of the patient's aorta. Once this positioning has been achieved, the proximal anchor member may be deployed so as to engage an inner surface of the patient's vasculature and anchor the proximal anchor member to the patient's aorta. Thereafter, the network of inflatable channels of the main graft member may be inflated with an inflation material so as to provide a more mechanically rigid structure. For some embodiments, a curable or hardenable fill material may be used that may be cured after inflation of the network of inflatable channels so as to provide additional mechanical rigidity as well as prevent leakage of the fill material. Some embodiments may also employ radiopaque inflation material to facilitate monitoring of the fill process and subsequent engagement of graft extensions.

A second delivery catheter containing a radially constrained self-expanding contralateral graft extension may then be axially positioned in the contralateral leg of the main graft member with a proximal portion of the contralateral graft extension axially overlapped with an inner fluid flow lumen of the contralateral leg of the main graft member and a distal portion of the contralateral graft extension axially overlapped with a portion of the patient's contralateral iliac artery. Access to the contralateral leg of the main graft portion may be achieved by percutaneous access or femoral arteriotomy from the patient's contralateral femoral artery with a delivery sheath or the like. Once properly positioned, the self-expanding contralateral graft extension may be deployed by releasing the radial constraint of the second delivery catheter. As the contralateral graft extension self expands in an outward radial orientation, a seal between the inner fluid flow lumen of the contralateral graft extension, a fluid flow lumen of the contralateral leg and a fluid flow lumen of the contralateral iliac artery may be formed.

A third delivery catheter containing a radially constrained self-expanding ipsilateral graft extension may then be axially positioned in the ipsilateral leg of the main graft member with a proximal portion of the ipsilateral graft extension axially overlapped with an inner fluid flow lumen of the ipsilateral leg of the main graft member and a distal portion of the ipsilateral graft extension axially overlapped with a portion of the patient's ipsilateral iliac artery. The self-expanding ipsilateral graft extension may then be deployed by releasing the radial constraint so as to form a seal between the inner fluid flow lumen of the ipsilateral graft extension, a fluid flow lumen of the ipsilateral leg and a fluid flow lumen of the ipsilateral iliac artery.

For some method embodiments of treating the vasculature of a patient, a modular graft assembly, such as the modular graft assembly embodiments 10 discussed above, may be used. FIGS. 7-14 illustrate an embodiment of a deployment sequence of an embodiment of a modular graft assembly. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter 75 may be directly inserted into the patient's access vessel by either arteriotomy or percutaneous puncture.

Once the delivery sheath or sheaths have been properly positioned, a delivery catheter 75 containing a modular graft assembly component, such as graft member 12, may then be advanced over a guidewire 76 through the delivery sheath and into the patient's vasculature. In one specific deployment method embodiment, the main graft member 12 is advanced within a delivery catheter 75 through the patient's vessel, typically in a proximal direction from the ipsilateral iliac artery, to a desired site of deployment, such as the abdominal aorta, in a constrained state via a catheter or like device having a low profile and lateral flexibility for ease of delivery through the patient's vasculature. At the desired site of deployment, the proximal anchor member 32 of the main graft 12 is released from a constrained state and the proximal anchor member 32 is allowed to expand and secure a portion of the main graft 12 to the patient's vasculature. Deployment of the modular graft assembly 10 may be carried out by any suitable devices and methods, including techniques and accompanying apparatus as disclosed in U.S. Pat. No. 6,761,733, entitled "Delivery Systems and Methods for Bifurcated Endovascular Graft" to Chobotov et al., filed on Jul. 27, 2001, and U.S. patent application Ser. No. 11/205,793, entitled "Delivery System and Method for Bifurcated Graft" to Chobotov et al., filed Aug. 15, 2005, which are incorporated by reference herein in their entirety.

Figure 7:
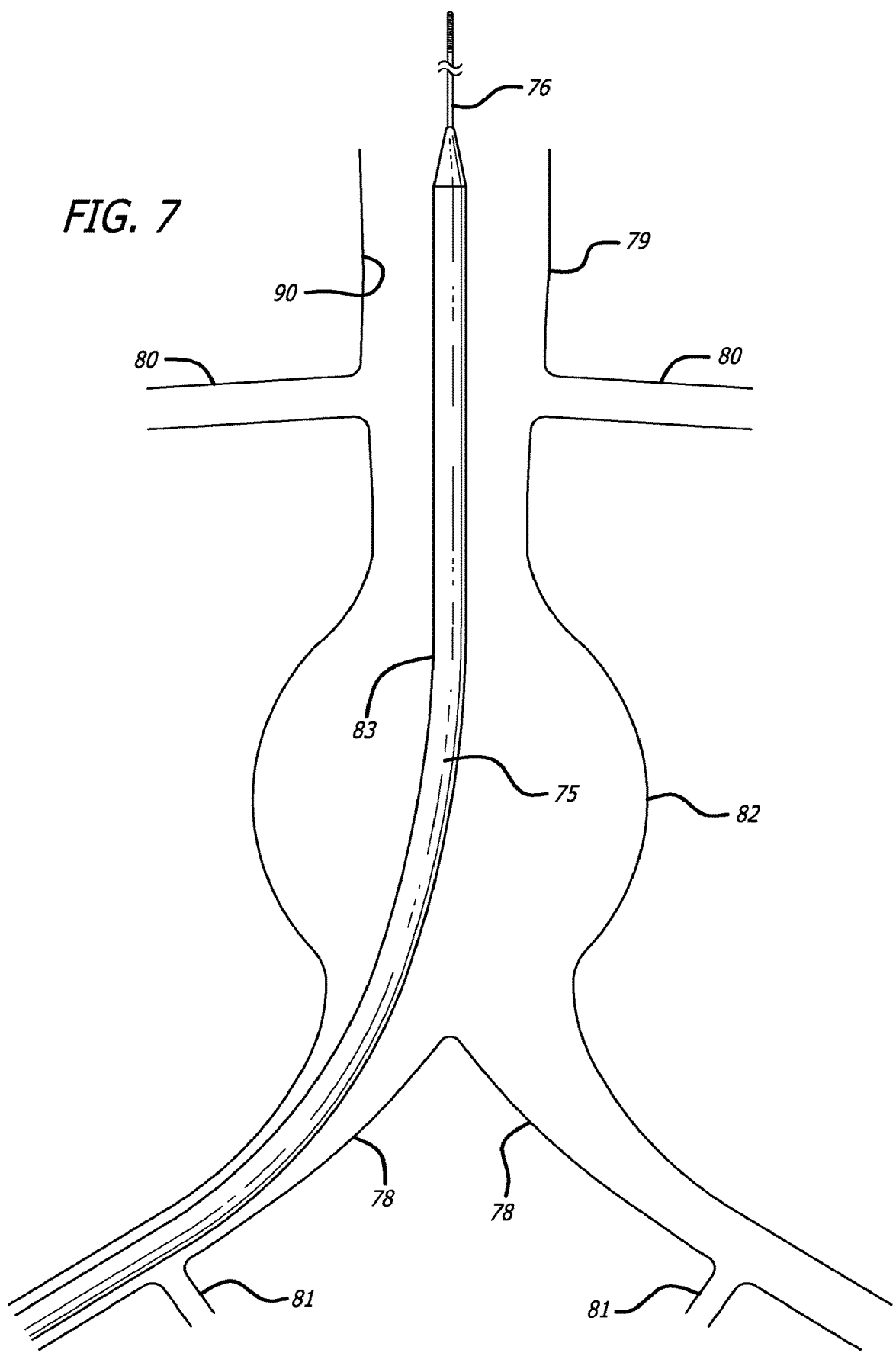
FIGS. 7-14 illustrate a deployment sequence of a modular graft system within the vasculature of a patient.
Figure 8:
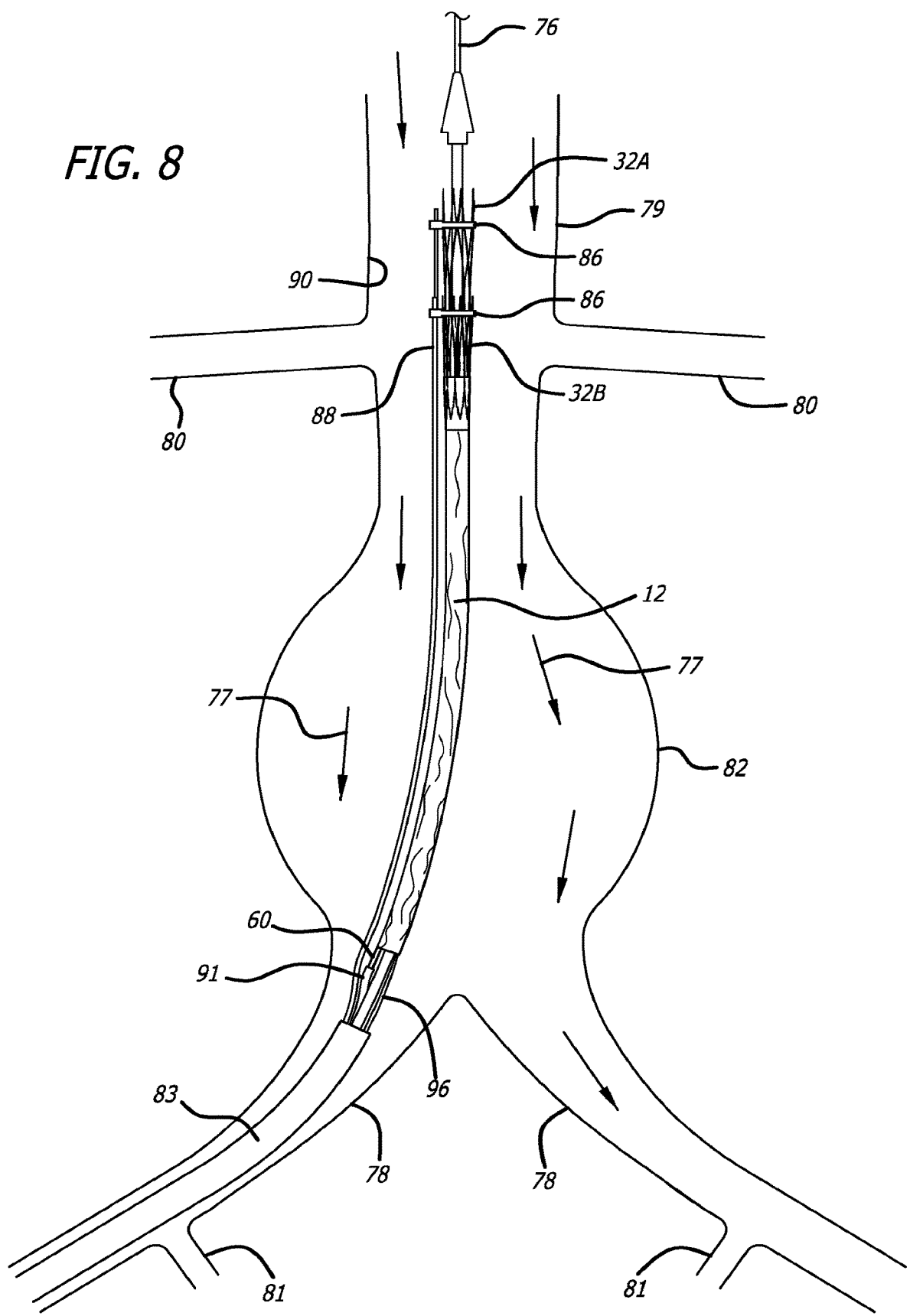

The delivery catheter 75 may be advanced proximally upstream of blood flow, as indicated by arrows 77, into the vasculature of the patient including the iliac artery 78 and aorta 79 shown in FIG. 7. Other vessels of the patient's vasculature shown in the figures include the renal arteries 80 and hypogastric arteries 81. The delivery catheter 75 may be advanced into the aorta 79 of the patient until the main graft 12 is disposed substantially adjacent an aortic aneurysm 82 or other vascular defect to be treated. Once the delivery catheter 75 is so positioned, an outer sheath 83 of the delivery catheter 75 may be retracted distally so as to expose the main graft 12 which has been compressed and compacted to fit within the inner lumen of the outer sheath 83 of the delivery catheter 75 as shown in FIG. 8. In addition to being radially compressed when disposed within an inner lumen of the outer sheath 83 of the delivery catheter 75, the proximal stent 32A and distal stent 32B have been radially restrained by respective high strength flexible belts 86 in order to maintain a small profile and avoid engagement of the stents 32A and 32B with a body lumen wall until deployment of the stents 32A and 32B is initiated. The ends of the belts 86 may be secured by one or more wires or elongate rods 88 which extend through looped ends of the belts 86. Once the outer sheath 83 of the delivery catheter 75 has been retracted, the delivery catheter 75 and graft assembly embodiment 10 may be carefully positioned in an axial direction such that the distal stent 32B is disposed substantially even with the renal arteries 80 with the proximal anchor member 32 and proximal sealing cuff 62 positioned proximal of the aneurysm 82. The proximal anchor member 32 is then deployed and anchored to the patient's aorta 79.

Figure 9:
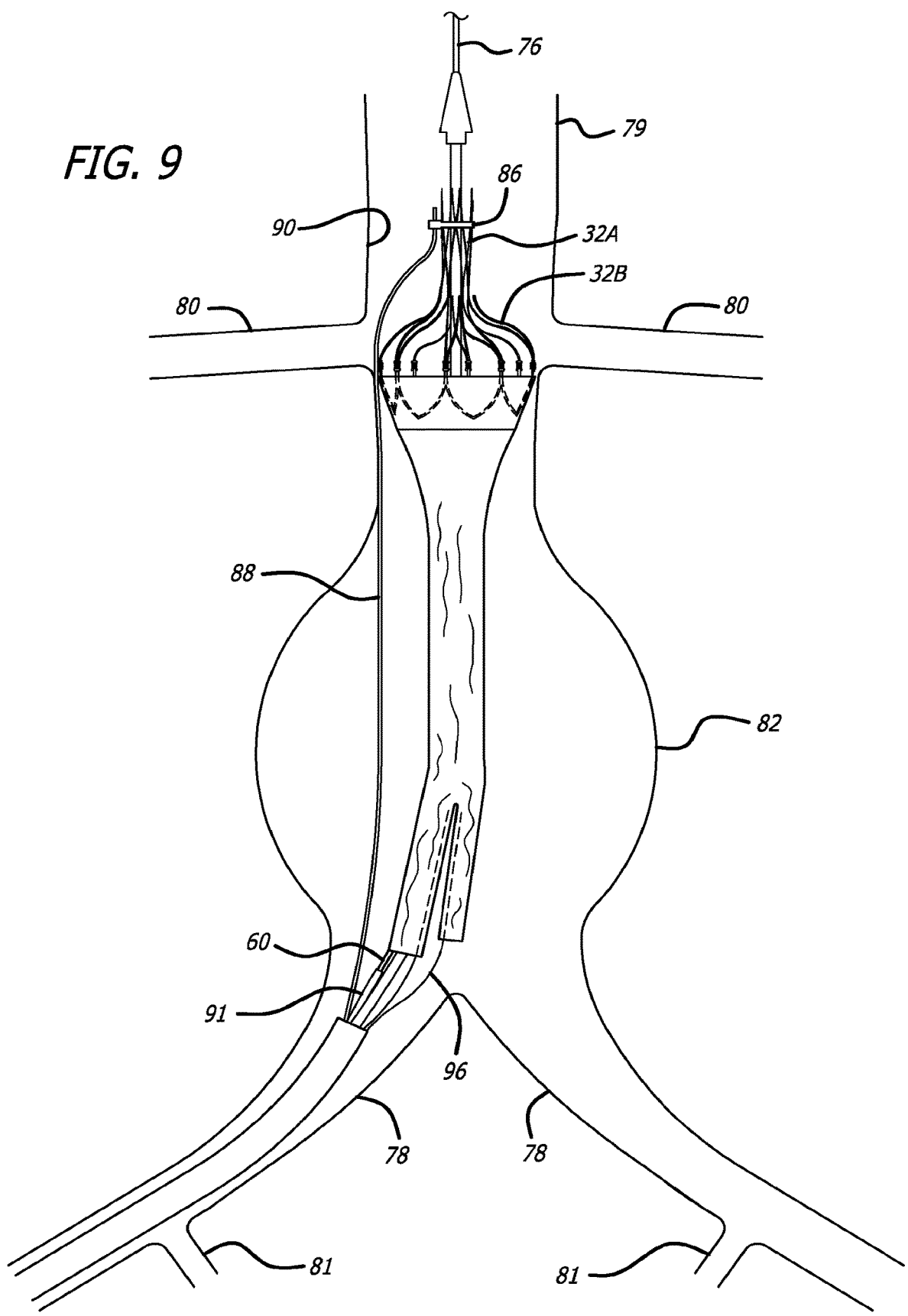

Deployment of the proximal anchor member 32 may begin with deployment of the distal stent 32B by retracting the wire or rod 86 that couples ends of belt 88 restraining distal stent 32B. Additional axial positioning may typically be carried out even after deploying the distal stent 32B of the proximal anchor member 32. This may still be carried out in many circumstances as the distal stent portion 32B of the distal anchor 32 does not include tissue engaging barbs 33 for some embodiments and will provide only partial outward radial contact or frictional force on the inner lumen of the patient's vessel 79 until the proximal stent 32A is deployed. Once the belt 86 constraining the distal stent 32B has been released, the distal stent 32B self-expands in an outward radial direction until an outside surface of the proximal stent 32B makes contact with and engages an inner surface 90 of the patient's vessel 79 as shown in FIG. 9.

Figure 10:
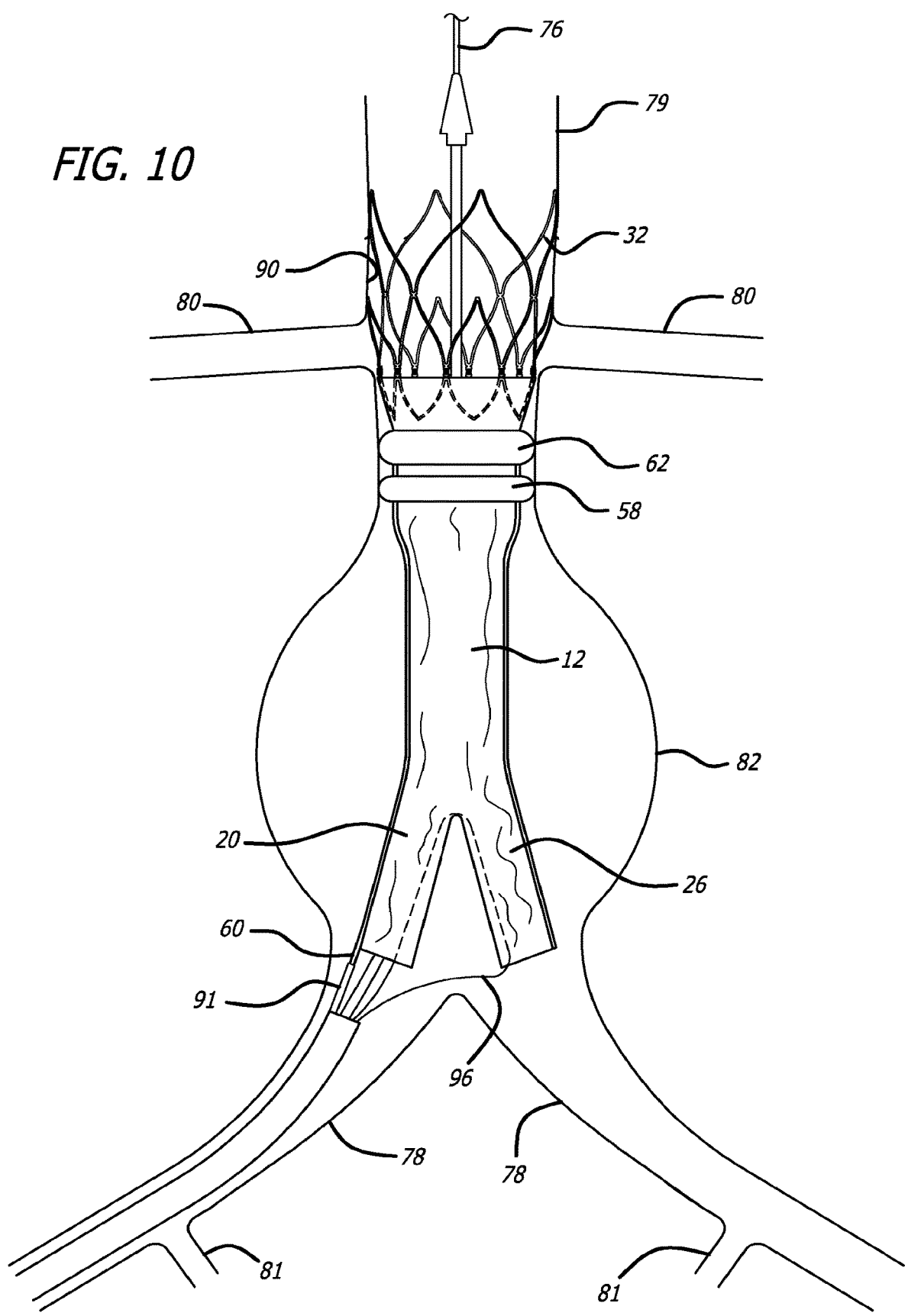

After the distal stent 32B has been deployed, the proximal stent 32A may then be deployed by retracting the wire 88 that couples the ends of the belt 86 restraining the proximal stent 32B. As the proximal stent 32A self-expands in an outward radial direction, an outside surface of the proximal stent 32A eventually makes contact with the inside surface 90 of the patient's aorta 79. For embodiments that include tissue engaging barbs 33 on the proximal stent 32A, the barbs may also be oriented and pushed in an outward radial direction so as to make contact and engage the inner surface tissue 90 of the patient's vessel 79, which further secures the proximal anchor member 32 to the patient's vessel 79 as shown in FIG. 10.

Figure 11:
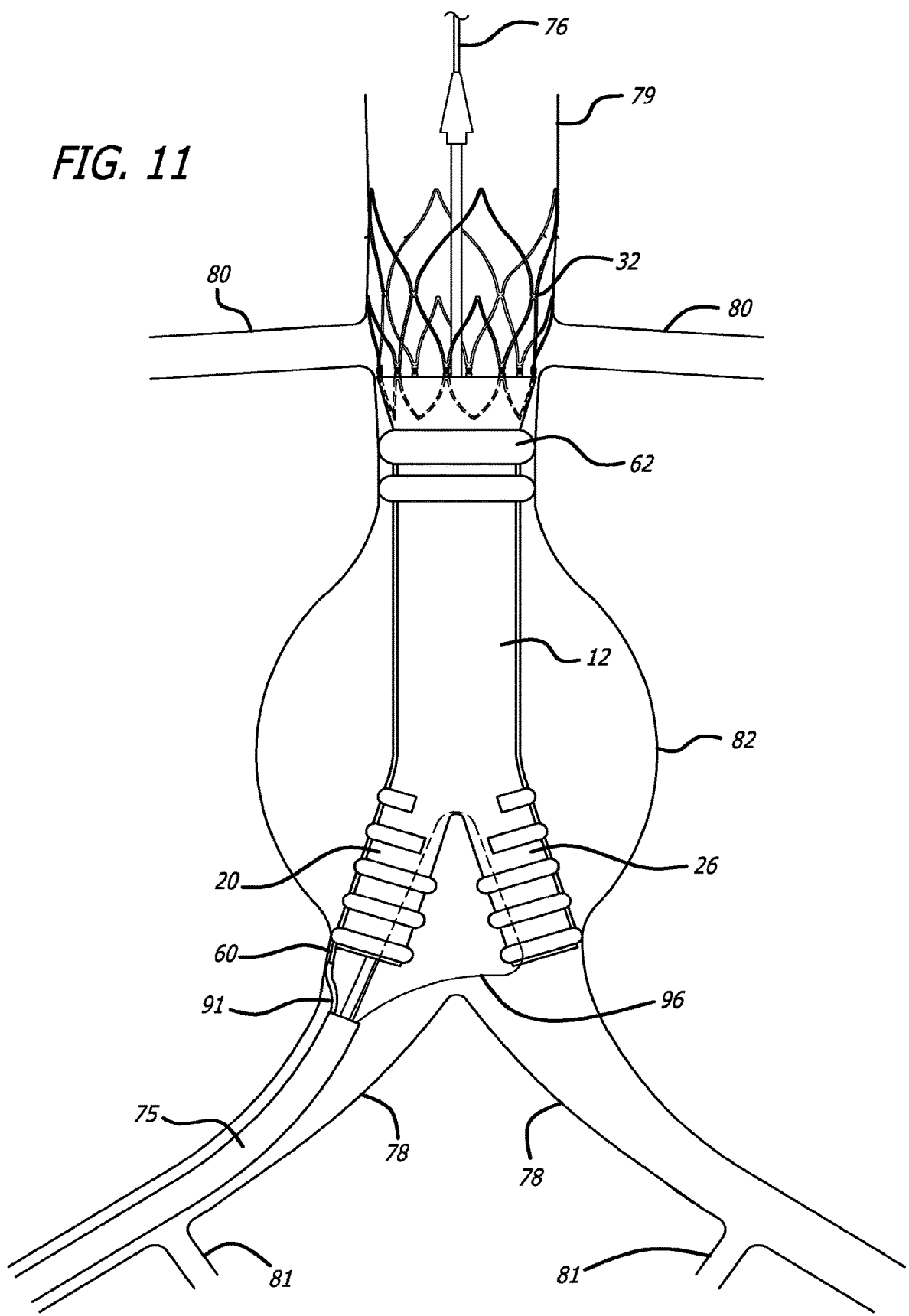

Once the proximal anchor member 32 has been secured to the inside surface 90 of the patient's vessel 79, the proximal inflatable cuff 62 may then be filled through the inflation port 60 with inflation material injected through an inflation tube 91 of the delivery catheter 75 which may serve to seal an outside surface of the inflatable cuff 62 to the inside surface 83 of the vessel 79. The remaining network of inflatable channels 58 are also filled with pressurized inflation material at the same time which provides a more rigid frame like structure to the graft 12 as shown in FIG. 11. For some embodiments, the inflation material may be a curable or hardenable material that may cured or hardened once the network of inflatable channels are filled to a desired level of material or pressure within the network. Some embodiments may also employ radiopaque inflation material to facilitate monitoring of the fill process and subsequent engagement of graft extensions. The material may be cured by any of the suitable methods discussed herein including time lapse, heat application, application of electromagnetic energy, ultrasonic energy application, chemical adding or mixing or the like.

The network of inflatable channels 58 may be partially or fully inflated by injection of a suitable inflation material into the main fill port 60 to provide rigidity to the network of inflatable channels 58 and the main graft 12. In addition, a seal is produced between the inflatable cuff 62 and the inside surface of the abdominal aorta 82. Although it is desirable to partially or fully inflate the network of inflatable channels 58 of the main graft 12 at this stage of the deployment process, such inflation step optionally may be accomplished at a later stage if necessary.

Figure 12:
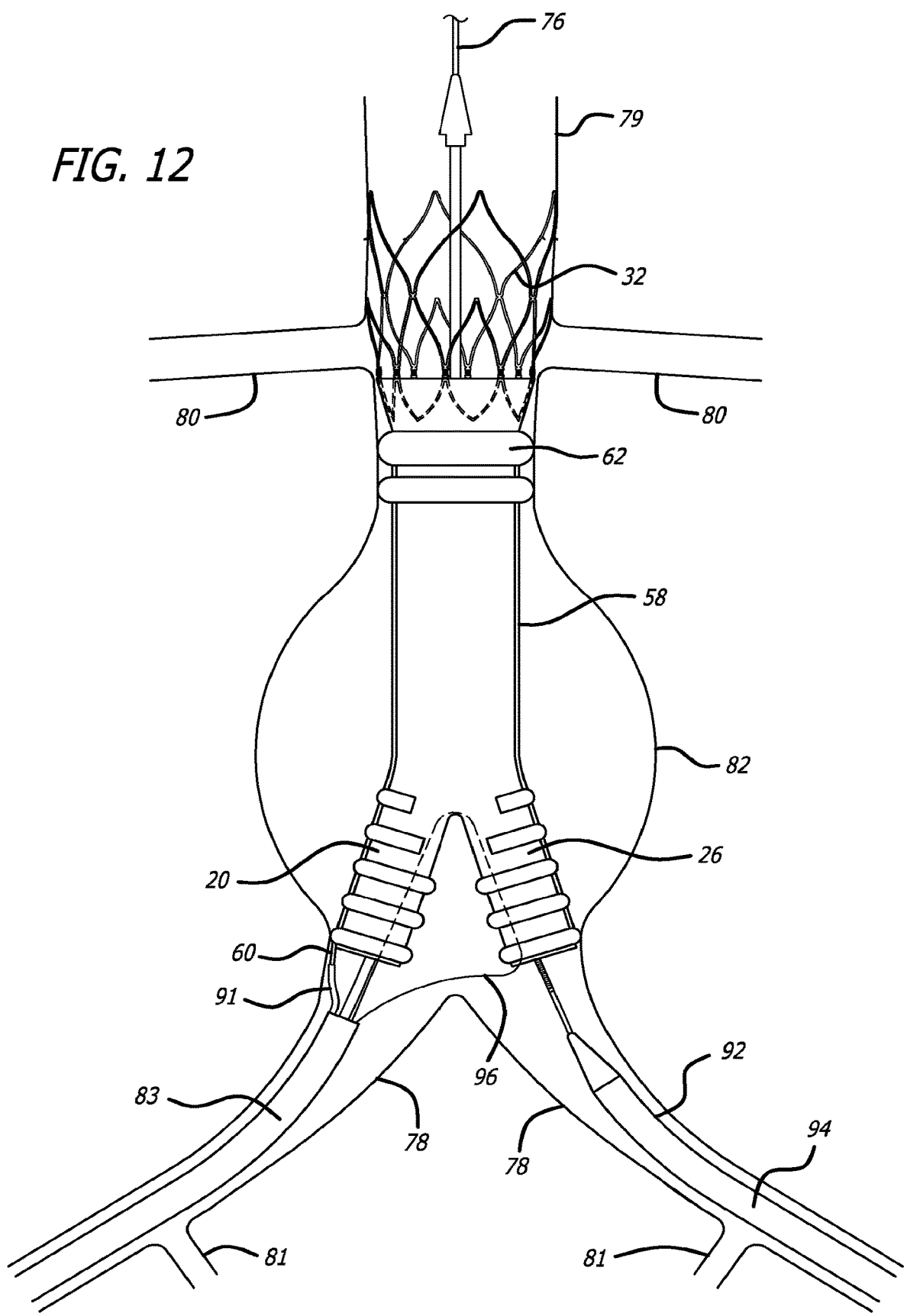

Once the graft member 12 is anchored and the inflatable channels 58 thereof have been filled and expanded, a second delivery catheter 92 that contains the contralateral graft extension 15 may access the contralateral femoral artery directly or through a delivery sheath as discussed above. The second delivery catheter may be advanced proximally, as shown in FIG. 12, until the radially compressed contralateral graft extension 15 is in an axial position which overlaps the contralateral leg 26 of the graft member 12. The amount of desired overlap of the graft extension 15 with the contralateral leg 26 may vary depending on a variety of factors including vessel morphology, degree of vascular disease, patient status and the like. However, for some embodiments, the amount of axial overlap between the contralateral graft extension 15 and the contralateral leg 26 may be about 1 cm to about 5 cm, more specifically, about 2 cm to about 4 cm. This overlapped position may also provide for longitudinal overlap between the fluid flow lumen 45 of the graft extension 15 with the fluid flow lumen of the contralateral leg 26.

Figure 13:
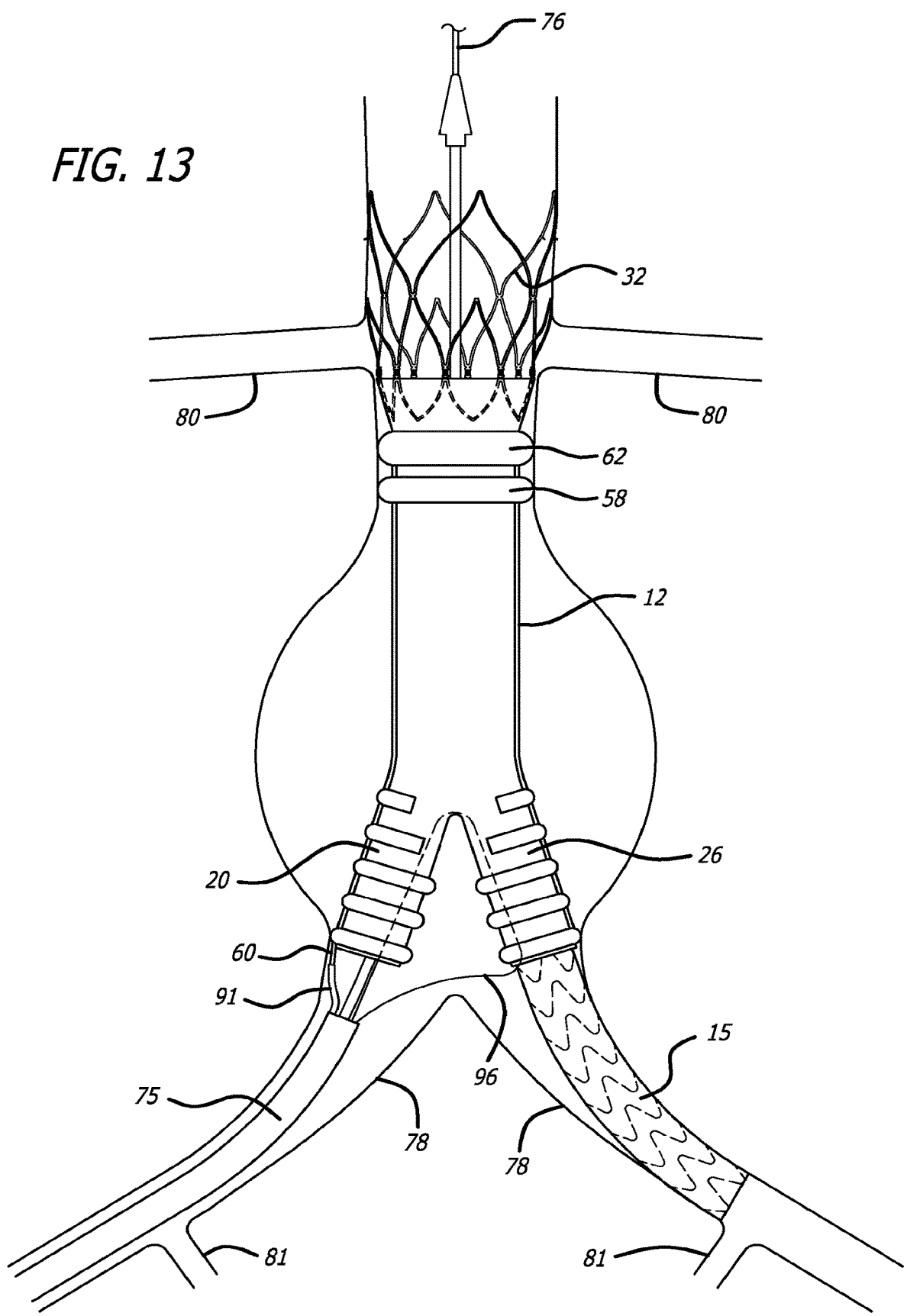

Once properly positioned, an outer sheath 94 of the second delivery catheter 92 which may radially restrain the contralateral graft extension 15, may be distally withdrawn while the graft extension 15 remains substantially axially fixed. This axial retraction of the outer sheath 94 of the second delivery catheter 92 deploys the contralateral graft extension 15 so as to allow the graft extension 15 to radially self-expand and engage the inner lumen 30 of the contralateral leg 26 and inner surface of the contralateral iliac artery proximal of the contralateral leg 26 as shown in FIG. 13. The graft extension 15 may be so deployed to extend the contralateral leg 20 of the main graft 12 with the inner lumen 30 of the contralateral leg 26 sealed to the inner lumen 45 of the graft extension 15. Once the contralateral graft extension 15 has been deployed, the second delivery catheter 92 may be withdrawn from the patient's vasculature.

Figure 14:
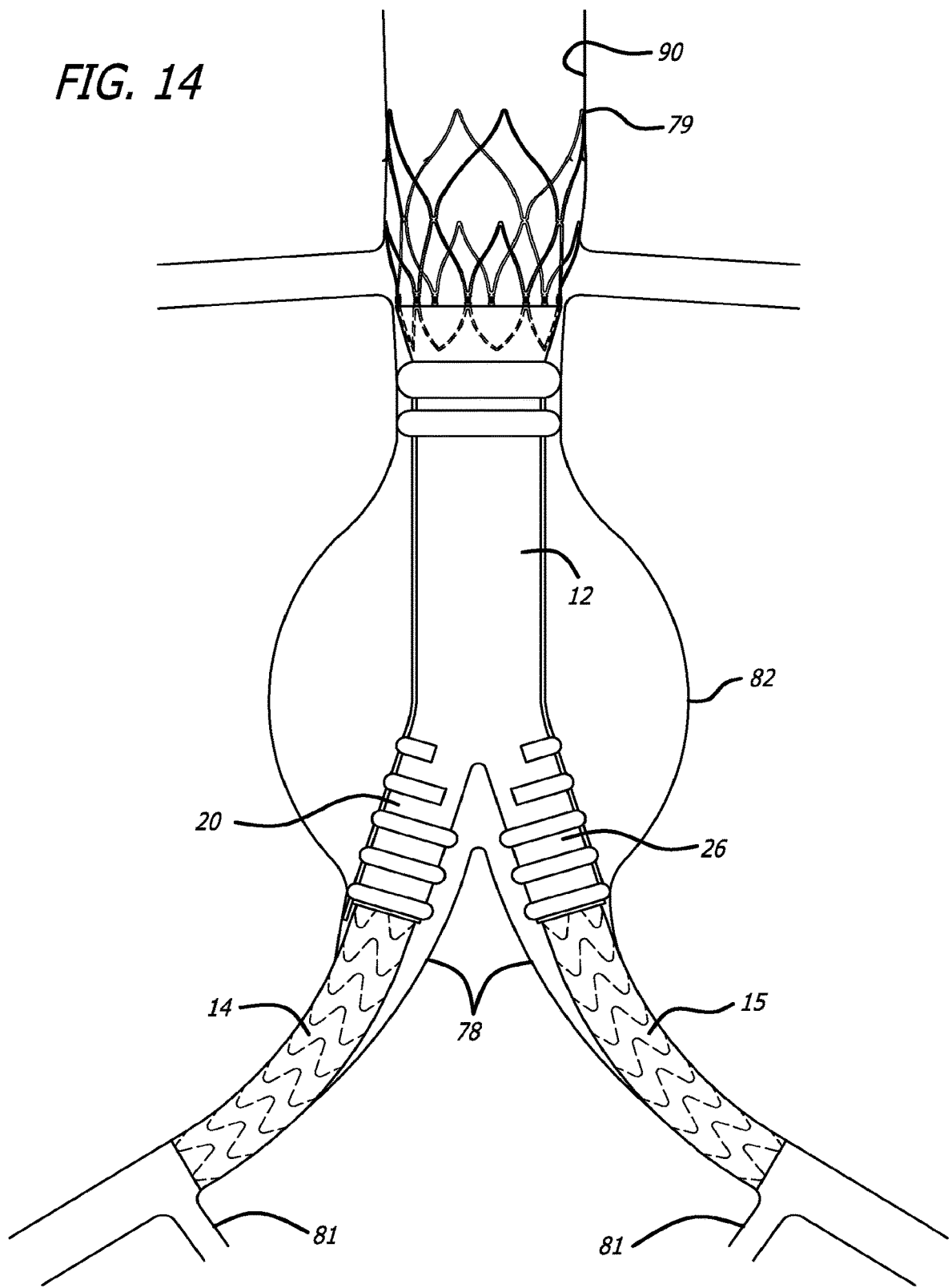

For some embodiments, up to the time that the network of inflatable channels 58 have been filled with inflation material which has been cured or hardened, an elongate tether 96 may be used to axially restrain the graft 12 and prevent axial separation of the graft 12 from the delivery catheter 75. This axial restraint may be important for embodiments wherein the inflation tube 91 of the delivery catheter 75 is secured to the fill port 60 of the network of inflatable channels 58 of the graft member 12 by an overlapped slip fit or interference fit only. For some embodiments, the inflation tube 91 may overlap with the fill tube 60 of the graft 12 by about 5 mm to about 25 mm, more specifically, about 10 mm to about 15 mm. The tether 96 loops through the flow lumens 24 and 30 of the ipsilateral and contralateral legs 20 and 26 of the graft member 12 and is secured to a handle on a proximal adapter (not shown) of the delivery catheter 75. The tether 96 is configured to have a length that is short enough to mechanically restrain distal axial movement of the main graft member 12 relative to the delivery catheter 75 so as to prevent decoupling of the inflation tube 91 from the inflation or fill port 60 of the main graft member 12. Once the inflation material has been fully injected into the network of inflatable channels 58 and cured or hardened, the tether 96 may be released and removed to allow distal retraction of the delivery catheter 75 as shown in FIG. 14.

Once the tether 96 has been released and the delivery catheter 75 retracted and decoupled from the graft main member 12 and patient's vasculature generally, a third delivery catheter (not shown) which contains the ipsilateral graft extension 14 may be advanced into the patient's vasculature directly or through an ipsilateral delivery sheath as discussed above. The third delivery catheter may have the same features, dimensions and materials as those of the second delivery catheter 92. The third delivery catheter may be advanced proximally through the patient's femoral artery and into the ipsilateral iliac artery 78 until the radially compressed ipsilateral graft extension 14 is in an axial position which overlaps the ipsilateral leg 20 of the graft member 12. Although not shown, this advancement of the third delivery catheter may be carried out in a manner which is the same as or similar to the deployment of the second delivery catheter 92 used for deployment of the contralateral graft extension 15 discussed above. The amount of desired overlap of the graft extension 14 with the ipsilateral leg 20 may once again vary depending on a variety of factors including vessel morphology, degree of vascular disease, patient status and the like. However, for some embodiments, the amount of axial overlap between the ipsilateral graft extension 14 and the ipsilateral leg 20 may be about 1 cm to about 5 cm, more specifically, about 2 cm to about 4 cm.

This overlapped position may also provide for longitudinal overlap between the fluid flow lumen 44 of the graft extension 14 with the fluid flow lumen 24 of the ipsilateral leg 20. Once properly positioned, an outer sheath of the third delivery catheter which may be configured to radially restrain the ipsilateral graft extension 14, may be distally withdrawn while the graft extension 14 remains substantially axially fixed. This axial retraction of the outer sheath of the third delivery catheter deploys the ipsilateral graft extension 14 so as to allow the graft extension 14 to radially self-expand and engage the inner lumen of the ipsilateral leg 20 and inner surface of the ipsilateral iliac artery proximal of the ipsilateral leg 20 as shown in FIG. 14. The extension 14 may be so deployed to extend the ipsilateral leg 20 of the main graft 12 with the inner lumen of the ipsilateral leg 20 sealed to the inner lumen 44 of the graft extension 14.

For some deployment embodiments, the patient's hypogastric arteries may be used to serve as a positioning reference point to ensure that the hypogastric arteries are not blocked by the deployment. Upon such a deployment, the distal end of a graft extension 14 or 15 may be deployed anywhere within a length of the ipsilateral or contralateral leg of the graft 12. Also, although only one graft extension is shown deployed on the ipsilateral side and contralateral side of the graft assembly 10, additional graft extensions 14 and 15 may be deployed within the already deployed graft extensions 14 and 15 in order to achieve a desired length extension of the ipsilateral leg 20 or contralateral leg 26. For some embodiments, about 1 to about 5 graft extensions 14 or 15 may be deployed on either the ipsilateral or contralateral sides of the graft assembly 10. Successive graft extensions 14 and 15 may be deployed within each other so as to longitudinally overlap fluid flow lumens of successive graft extensions.

Figure 15:
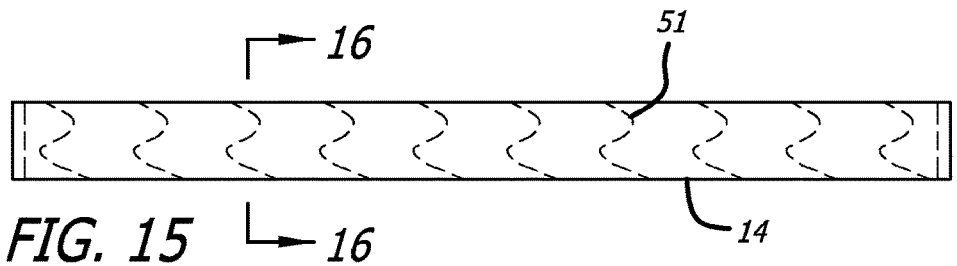
FIG. 15 is an elevation view of an embodiment of a graft extension.

Graft extensions 14 and 15, which may be interchangeable for some embodiments, or any other suitable extension devices or portions of the main graft section 12 may include a variety of suitable configurations. For some embodiments, graft extensions 14 and 15 may include a PTFE covered helical nitinol stent 51 as discussed above with layers of PTFE having a variety of characteristics. Regarding the stent 51, it may be formed from an elongate resilient element which is helically wound with a plurality of longitudinally spaced turns. Some stent embodiments 51 may be generally helical in configuration with serpentine or other regularly space undulations transverse to the helical path of the elongate stent element as shown in more detail in FIG. 15. The ends of the stent element may be secured to adjacent ring portions of the stent 51 as shown to avoid exposure of element ends to either PTFE graft material or possible patient tissues. The stent element of the stent 51 shown in FIG. 15 is a continuous element from one end of the extension 14 to the other end thereof. The ends of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch.

Figure 16:
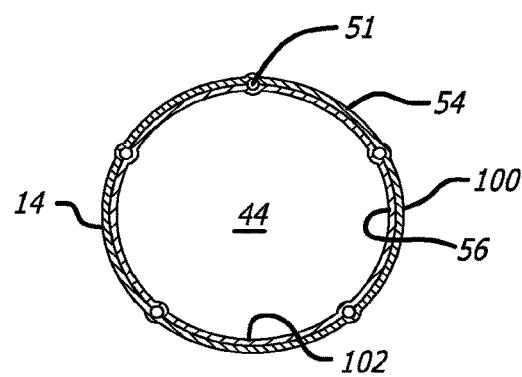
FIG. 16 is a transverse cross sectional view of the graft extension of FIG. 15 taken along lines 16-16 of FIG. 15.

For some embodiments of graft extension 14, layers of materials having different properties may be used in combination to achieve a desired clinical performance. For example, some layers of PTFE covering the stent 51 may be permeable, semi-permeable or substantially non-permeable depending on the desired performance and material properties. FIG. 16 illustrates a transverse cross sectional view of an embodiment of extension 14 of FIG. 15 that shows an outer layer of PTFE 54 and an inner layer of PTFE 56. The layers 54 and 56 may be applied by a variety of methods and have a variety of configurations. For example, some layer embodiments may include extruded tubular structures applied axially over a mandrel or subassembly. Some layer embodiments 54 and 56 may be applied by wrapping layers circumferentially or wrapping tapes or ribbons in an overlapping helical pattern. For some embodiments, the outer layer 54 may be made from or include a semi-permeable or substantially non-permeable PTFE layer 100 and the inner layer 56 may be made of or include a permeable layer of PTFE 102.

The extension 14 may be made by forming the layers of material 100 and 102 together with the stent 51 over a mandrel, such as a cylindrical mandrel (not shown). Once the innermost layer 102 of the extension 14 has been wrapped about a shaped mandrel, a helical nitinol stent, such as helical stent 51, may be placed over the innermost layered PTFE layer 56 and underlying mandrel. One or more additional layers of low permeability PTFE film or PTFE film having substantially no permeability 100 that does not have the traditional node fibril microstructure may be wrapped or otherwise added over the exterior of the stent 51. The mandrel may then be covered with a flexible tube such that the film and stent is sandwiched under pressure and sintered so as to raise the temperature for the PTFE material to undergo a melt transformation in order to lock in its geometry and strength. The flexible tube (a manufacturing aid not shown) is removed from over the device and the resultant extension is removed from the mandrel.

FIG. 16 illustrates the layered structure of an extension embodiment 14 that has been conformed to a mandrel with the layers of PTFE material over the stent conforming to the stent element so as to form a cohesive structure. In addition, for some embodiments, an adhesives such as FEP or the like may be applied adjacent the stent prior to the application of the PTFE layer covering the stent, or at any other suitable time or location, in order to facilitate a bond between the stent element and the PTFE materials 100 and 102 adjacent the stent 51. For the embodiment of extension 14 shown in FIG. 16, the extension may have the same features, dimensions and materials as those discussed above with regard to the extension embodiment 14 shown in FIGS. 1-6. For some embodiments, the permeable PTFE material 102 may include an ePTFE material having uniaxial expansion with a uniaxial node fibril structure. PTFE materials having a multiaxial node fibril orientation may also be used for some embodiments. For some embodiments, the permeable material 102 may include about 1 to about 5 layers of material or more and have an inter nodal distance of about 10 microns to about 30 microns. The permeable material 102 may have a thickness for some embodiments of about 0.00005 inch to about 0.005 inch.

For some embodiments, the low permeability non-expanded PTFE material 100 may have a non-typical node fibril microstructure with essentially no nodal spacing and very low or no liquid permeability. The extensions 14 and 15 may include about 1 layer to about 5 layers of semi-permeable or substantially non-permeable PTFE material having a thickness of about 0.0001 inches to about 0.005 inches, more specifically, about 0.0004 inches to about 0.001 inches. Examples of such materials are described in U.S. Patent Application publication numbers 2006/0233990 and 2006/0233991 described above which are incorporated by reference in their entirety herein.

For some embodiments, the PTFE material 100 having low permeability or substantially no permeability may be made by providing a PTFE layer and applying a stretching agent, such as an isopar lubricant material, to at least a portion of the PTFE layer and stretching the PTFE layer while the layer is wet with stretching agent. For some embodiments, the PTFE layer may be saturated with stretching agent while being stretched. For some embodiments, the PTFE layer may be stretched by a ratio of about 2:1 to about 20:1. For some embodiments, the wet stretching of the PTFE layer is carried out in a direction transverse to the machine direction of expansion. For some embodiments, the wet stretching of the PTFE layer is carried out at a temperature of about 80 degrees F. to about 130 degrees F., or at a temperature that is just above the glass transition temperature of the PTFE layer material. For some embodiments, the PTFE layer provided is made by extruding a compounded PTFE resin through an extruder to form a PTFE ribbon extrudate. Such a PTFE material 100 may have substantially low porosity, low permeability, no discernable node and fibril structure and a thickness of about 0.00005 inch to about 0.005 inch. Some such PTFE materials may also have a closed cell microstructure with a plurality of interconnected high density regions having no discernable node and fibril structure between the high density regions. Some such PTFE materials may have low or no fluid permeability.

Figure 4:
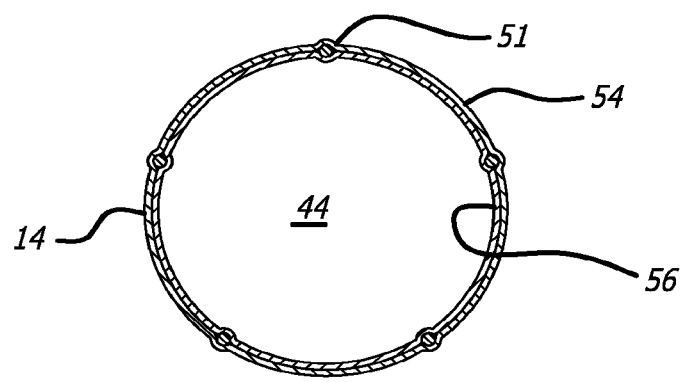
FIG. 4 is a transverse cross section of the graft extension of the modular graft assembly of FIG. 1 taken along lines 4-4 of FIG. 1.
Figure 4A:
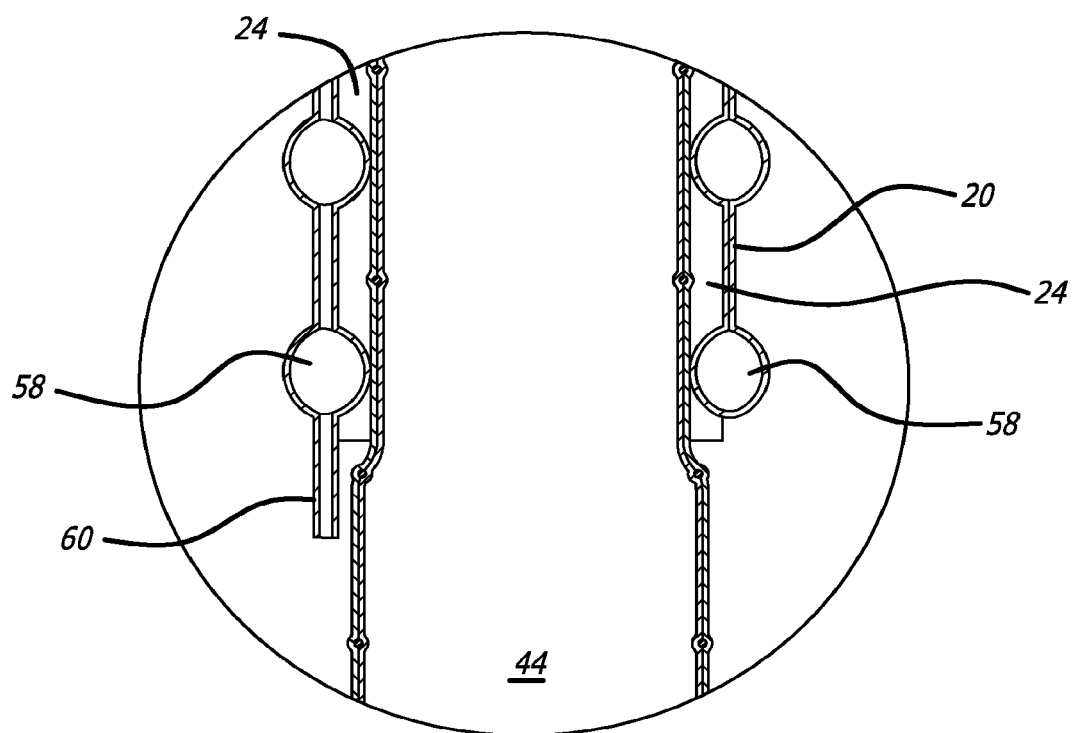
FIG. 4A is an enlarged view of a junction between a graft extension and an ipsilateral leg of the graft assembly of FIG. 1 indicated by the encircled portion 4A-4A in FIG. 1.

FIGS. 17A-17E illustrate schematic representations of several useful extension configurations 14 in transverse cross section that may have the same or similar materials, dimensions and features compared to those of the embodiment shown in FIG. 16 and the embodiment shown in FIG. 4 above. The cross sections shown do not indicate the conformal nature of the PTFE layers with the stent structure as shown in FIG. 16, but are meant to show the number, location and types of PTFE layers with respect to stent 51 for particular embodiments of extensions 14 and 15 and any other suitable extension embodiments, however, the conformal configuration of FIG. 16 may be produced in these embodiments by the methods discussed above. The embodiments of FIGS. 17A-17E are directed to extensions 14 that have low permeability or substantially no permeability and good structural integrity, particularly in areas where the PTFE layer material or materials meet the stent 51.

Figure 17A:
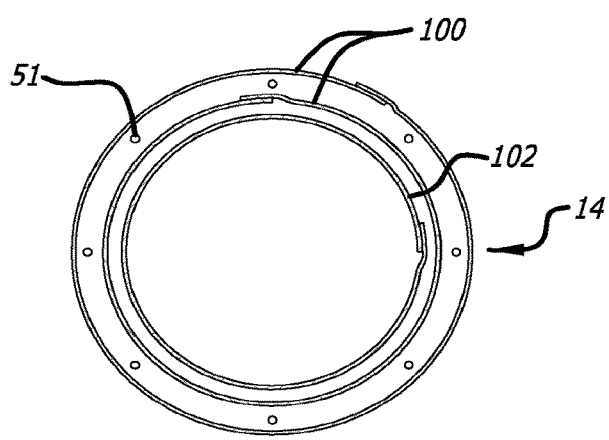
FIGS. 17A to 17E illustrate embodiments of graft extension configurations.
Figure 17B:
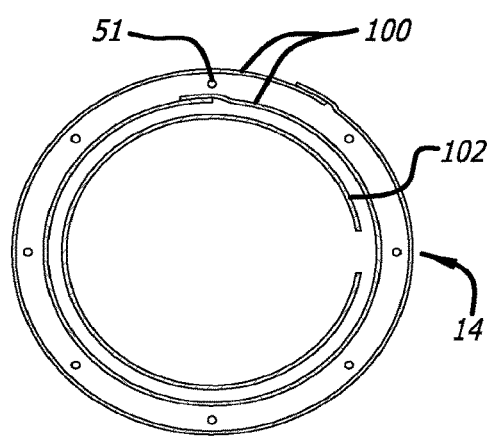

FIG. 17A illustrates an extension configuration 14 having one or more inner layers of permeable PTFE material 102 and one or more layers of semi-permeable or substantially non-permeable PTFE material 100 disposed between the inner layer and the stent 51. One or more layers of semi-permeable or substantially non-permeable PTFE material is disposed outside the stent 51. Each of the layers of PTFE material has been wrapped, either circumferentially or helically, about itself to form a continuous tubular structure with overlapping ends or edges. FIG. 17B illustrates an extension configuration that is substantially the same as that of FIG. 17A, except that the inner most layer or layers of PTFE material 102 do not connect along a longitudinal or helical line extending from one end of the extension 14 to the other end of the extension 14 as indicated by the gap in the inner most layer or layers shown in the FIG. 17B. As such, the inner most layer or layers of extension embodiment 14 of FIG. 17B forms a generally tubular structure, but it is not a closed or complete tubular structure. The tubular structures formed by the permeable material 102 in FIGS. 17A and 17B may have the node fibril direction of the material oriented substantially along the longitudinal axis of the extension 14 for some embodiments.

Figure 17C:
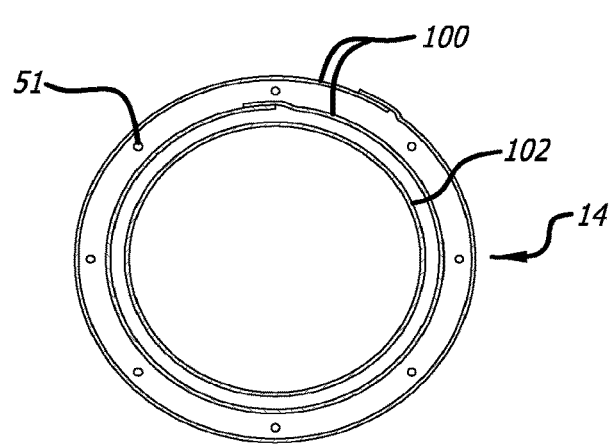
Figure 17D:
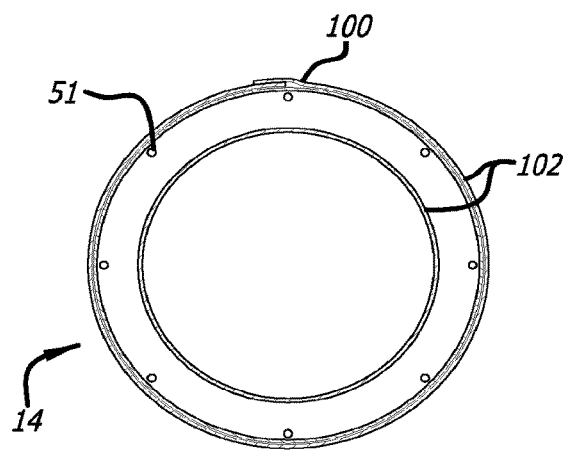
Figure 17E:
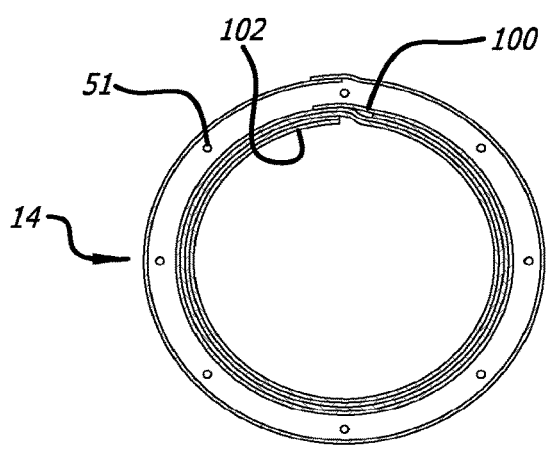

FIG. 17C illustrates an extension configuration 14 that is also substantially the same as that of FIG. 17A, except that the inner most layer or layers of permeable PTFE material are configured as a continuous extruded tubular structure as opposed to the wrapped structure indicated for the embodiments in FIGS. 17A and 17B. The layer or layers of semi-permeable or substantially non-permeable material 100 on either side of the stent 51 are shown with a helically or circumferentially wrapped structure with overlapping ends to form a continuous and closed tubular structure. FIG. 17D illustrates an extension configuration 14 having an extruded tubular inner most layer of permeable material 102 on the inside of the stent 51 and a similar layer of extruded tubular permeable PTFE material 102 on the opposite side of the stent 51. The layer or layers of extruded tubular permeable material 102 form respective closed and continuous tubular structures on either side of the stent 51. A layer or layers of semi-permeable or substantially non-permeable material 100 is disposed over the outer layer of permeable material 102 and is wrapped either circumferentially or helically with overlapping ends to form a closed tubular structure.

FIG. 17 E illustrates an extension configuration embodiment 14 having an inner tubular structure formed from a layer or adjacent layers of a semi-permeable or substantially non-permeable material 100 disposed adjacent a layer or adjacent layers of permeable material 102 which have been wrapped together to form a continuous and closed tubular structure disposed within the stent 51. The circumferential ends or edges of the layer of semi-permeable or substantially non-permeable material 100 extend circumferentially beyond the circumferential ends or edges of the permeable material 102. As such, the inner wrapped layers, which may be wrapped either helically or circumferentially, are arranged such that the permeable layer 102 never makes contact with itself or the stent 51.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A modular endovascular graft assembly, comprising:
    a bifurcated main graft member formed from a supple graft material including a main fluid flow lumen therein, an ipsilateral leg with an ipsilateral fluid flow lumen in communication with the main fluid flow lumen, and a contralateral leg with a contralateral fluid flow lumen in communication with the main fluid flow lumen;
    a proximal anchor member which is formed from a single piece of material, which is disposed at a proximal end of the main graft member, which is secured to the main graft member and which includes a self-expanding proximal stent portion, a self-expanding distal stent portion, and struts that are disposed between adjacent crowns of the proximal stent portion and the distal stent portion, each strut of said struts including a cross sectional area that is the same as or greater than a respective cross sectional area of either the proximal stent portion or the distal stent portion adjacent the strut at locations of connection of the strut to the proximal stent portion and the distal stent portion, and each strut of the struts extending integrally between the proximal stent portion and the distal stent portion such that the strut is continuous with the proximal stent portion and the distal stent portion as part of the single piece of material;
at least one ipsilateral graft extension including a fluid flow lumen disposed therein with the fluid flow lumen of the ipsilateral graft extension sealed to and in fluid communication with the fluid flow lumen of the ipsilateral leg of the main graft member; and
at least one contralateral graft extension including a fluid flow lumen disposed therein with the fluid flow lumen of the contralateral graft extension sealed to and in fluid communication with the fluid flow lumen of the contralateral leg of the main graft member.

2. The graft assembly of claim 1, wherein the main graft member has an axial length of about 5 cm to about 10 cm.

3. The graft assembly of claim 2, wherein the main graft member has an axial length of about 6 cm to about 8 cm.

4. The graft assembly of claim 1, wherein each strut of the struts extends from a respective apex of the proximal stent portion and into a respective apex of the distal stent portion and is located entirely between the respective apex of the proximal stent portion and the respective apex of the distal stent portion.

5. The graft assembly of claim 1, wherein the proximal stent portion of the proximal anchor member further comprises a plurality of barbs having sharp tissue engaging tips that are configured to extend in a radial outward direction in a deployed expanded state.

6. The graft assembly of claim 1, wherein the supple graft material comprises layered porous or expanded PTFE.

7. The graft assembly of claim 1, wherein the ipsilateral graft extension comprises an interposed self-expanding stent disposed between at least one outer layer and at least one inner layer of supple layers of graft material and wherein the interposed stent disposed between the outer layer and inner layer of graft material is formed from an elongate resilient element helically wound with a plurality of longitudinally spaced turns into an open tubular configuration.

8. The graft assembly of claim 7, wherein the interposed stent is comprised of a superelastic alloy.

9. The graft assembly of claim 8, wherein the superelastic alloy comprises superelastic NiTi alloy.

10. The graft assembly of claim 7, wherein the graft material of the ipsilateral graft extension further comprises at least one axial zone of low permeability.

11. The graft assembly of claim 1, wherein the proximal stent portion of the proximal anchor member comprises a 4 crown stent.

12. The graft assembly of claim 1, wherein the distal stent portion of the proximal anchor member comprises an 8 crown stent.

13. The graft assembly of claim 1, wherein the proximal stent portion and distal stent portion of the proximal anchor member comprise a superelastic alloy.

14. The graft assembly of claim 13, wherein the superelastic alloy comprises superelastic NiTi alloy.

15. The graft assembly of claim 13, further comprising a network of inflatable channels disposed on the main graft member including the ipsilateral and contralateral legs which is configured to accept a fill material to provide structural rigidity to the main graft member when the network of inflatable channels are in an inflated state and which includes at least one inflatable cuff disposed on a proximal portion of the main graft member configured to seal against an inside surface of a patient's vessel.

16. An endovascular graft assembly, comprising:
a main graft member formed from a supple graft material including a main fluid flow lumen therein; and
a proximal anchor member which is formed from a single piece of material, which is disposed at a proximal end of the main graft member, which is secured to the main graft member and which includes a self-expanding proximal stent portion, a self-expanding distal stent portion, and struts that are disposed between adjacent crowns of the proximal stent portion and the distal stent portion, each strut of said struts including a cross sectional area that is the same as or greater than a respective cross sectional area of either the proximal stent portion or the distal stent portion adjacent the strut at locations of connection of the strut to the proximal stent portion and the distal stent portion, and each strut of the struts extending integrally between the proximal stent portion and the distal stent portion such that the strut is continuous with the proximal stent portion and the distal stent portion as part of the single piece of material.

17. The graft assembly of claim 16, wherein the proximal stent portion of the proximal anchor member further comprises a plurality of barbs having sharp tissue engaging tips that are configured to extend in a radial outward direction in a deployed expanded state.

18. The graft assembly of claim 16, wherein the supple graft material of the main graft member comprises layered porous or expanded PTFE.

19. The graft assembly of claim 16, wherein the supple graft material of the main graft member comprises DACRON.

20. The graft assembly of claim 16, wherein the proximal stent portion and distal stent portion of the proximal anchor member comprise a superelastic alloy.

21. A modular endovascular graft assembly, comprising:
a bifurcated main graft member formed from a supple graft material including a main fluid flow lumen therein, an ipsilateral leg with an ipsilateral fluid flow lumen in communication with the main fluid flow lumen, and a contralateral leg with a contralateral fluid flow lumen in communication with the main fluid flow lumen; and
a proximal anchor member which is formed from a single piece of material, which is disposed at a proximal end of the main graft member, which is secured to the main graft member and which includes a self-expanding proximal stent portion, a self-expanding distal stent portion, and struts that are disposed between adjacent crowns of the proximal stent portion and the distal stent portion, each strut of said struts including a cross sectional area that is the same as or greater than a cross sectional area of either the proximal stent portion or the distal stent portion adjacent the strut at locations of connection of the strut to the proximal stent portion and the distal stent portion, and each strut of the struts extending integrally between the proximal stent portion and the distal stent portion such that the strut is continuous with the proximal stent portion and the distal stent portion as part of the single piece of material.

22. A proximal anchor member for anchoring an endovascular graft, comprising:
  a self-expanding proximal stent portion;
  a self-expanding distal stent portion; and
  one or more struts which are disposed between adjacent crowns of the proximal stent portion and the distal stent portion, each strut of said one or more struts including a cross sectional area that is the same as or greater than a cross sectional area of either the proximal stent portion or the distal stent portion adjacent the strut at locations of connection of the strut to the proximal stent portion and the distal stent portion, and each strut of the one or more struts extending integrally between the proximal stent portion and the distal stent portion such that the strut is continuous with the proximal stent portion and the distal stent portion as part of a single piece of material.

* * * * *